United States Patent
Bykova et al.

(10) Patent No.: US 10,864,301 B2
(45) Date of Patent: Dec. 15, 2020

(54) FABRICATING A CARBON NANOFIBER YARN NERVE SCAFFOLD

(71) Applicant: Lintec Of America, Inc., Richardson, TX (US)

(72) Inventors: Julia Bykova, Richardson, TX (US); Marcio D. Lima, Richardson, TX (US); Kanzan Inoue, Phoenix, AZ (US)

(73) Assignee: LINTEC OF AMERICA, INC., Richardson, TX (US)

( * ) Notice: Subject to any disclaimer, the term of this patent is extended or adjusted under 35 U.S.C. 154(b) by 0 days.

(21) Appl. No.: 16/353,608

(22) Filed: Mar. 14, 2019

(65) Prior Publication Data

US 2019/0282733 A1    Sep. 19, 2019

Related U.S. Application Data

(60) Provisional application No. 62/643,496, filed on Mar. 15, 2018, provisional application No. 62/758,035, filed on Nov. 9, 2018.

(51) Int. Cl.

| | | |
|---|---|---|
| A61L 27/42 | (2006.01) | |
| A61L 27/38 | (2006.01) | |
| D02G 3/40 | (2006.01) | |
| A61L 31/02 | (2006.01) | |
| D02G 3/02 | (2006.01) | |
| B82Y 5/00 | (2011.01) | |
| D02G 3/44 | (2006.01) | |
| C01B 32/158 | (2017.01) | |
| A61B 17/11 | (2006.01) | |
| D02G 1/02 | (2006.01) | |
| B82Y 40/00 | (2011.01) | |

(52) U.S. Cl.
CPC ........ *A61L 27/422* (2013.01); *A61B 17/1128* (2013.01); *A61L 27/3878* (2013.01); *A61L 31/024* (2013.01); *B82Y 5/00* (2013.01); *C01B 32/158* (2017.08); *D02G 1/0206* (2013.01); *D02G 3/02* (2013.01); *D02G 3/40* (2013.01); *D02G 3/448* (2013.01); *A61B 2017/1132* (2013.01); *A61L 2400/12* (2013.01); *B82Y 40/00* (2013.01); *D10B 2101/122* (2013.01); *D10B 2509/00* (2013.01); *D10B 2509/04* (2013.01)

(58) Field of Classification Search
None
See application file for complete search history.

(56) References Cited

U.S. PATENT DOCUMENTS

| | | |
|---|---|---|
| 3,528,874 A | 9/1970 | Spencer |
| 9,402,724 B2 | 8/2016 | Day et al. |
| 9,572,909 B2 | 2/2017 | Simpson et al. |
| 2006/0159718 A1 | 7/2006 | Rathenow et al. |
| 2007/0269481 A1 | 11/2007 | Li et al. |
| 2008/0208358 A1 | 8/2008 | Bellamkonda et al. |
| 2009/0275960 A1 | 11/2009 | Provenza et al. |
| 2010/0075904 A1 | 3/2010 | Laurencin et al. |
| 2013/0035767 A1 | 2/2013 | Fan et al. |
| 2015/0147573 A1* | 5/2015 | Zhang ................... B82Y 10/00 428/408 |

FOREIGN PATENT DOCUMENTS

| | | |
|---|---|---|
| EP | 1803844 A1 | 7/2007 |
| KR | 20150007576 A | 1/2015 |
| WO | 2016192733 A1 | 12/2016 |

OTHER PUBLICATIONS

International Search Report and Written Opinion received for PCT/US2019/022515, dated May 31, 2019. 10 pages.
Bogdanovich, Alexander E. and Bradford, Philip D., "Carbon nanotube yarn and 3-D braid composites. Part I: Tensile testing and mechanical properties analysis," Elsevier, Composites: Part A 41 (2010). pp. 230-237.
Huang, et al., "Effects of laminin-coated carbon nanotube/chitosan fibers on guided neurite growth," J Biomed Mater Res Part A 2011. pp. 86-93.
International Search Report and Written Opinion received for PCT/US2019/022274, dated Jun. 3, 2019. 8 pages.

* cited by examiner

*Primary Examiner* — Jake M Vu
(74) *Attorney, Agent, or Firm* — Greenblum & Bernstein, P.L.C.

(57) ABSTRACT

Nerve scaffolds are described that include a tubular outer housing fabricated from a biocompatible polymer, within which are disposed a plurality of carbon nanofiber yarns. The carbon nanofiber yarns, which can be separated by distances roughly corresponding to an average nerve fiber diameter, provide surfaces on which nerve fibers can regrow. Because the proximate carbon nanofiber yarns can support individual nerve fibers, a nerve can be regenerated with a reduced likelihood of undesirable outcomes, such as nerve pain or reduced nerve function.

19 Claims, 15 Drawing Sheets

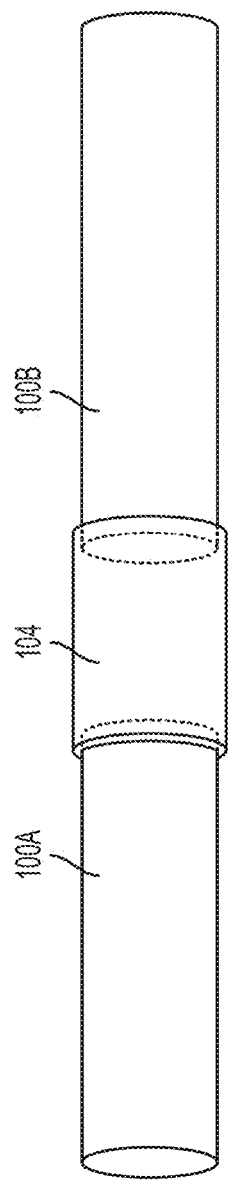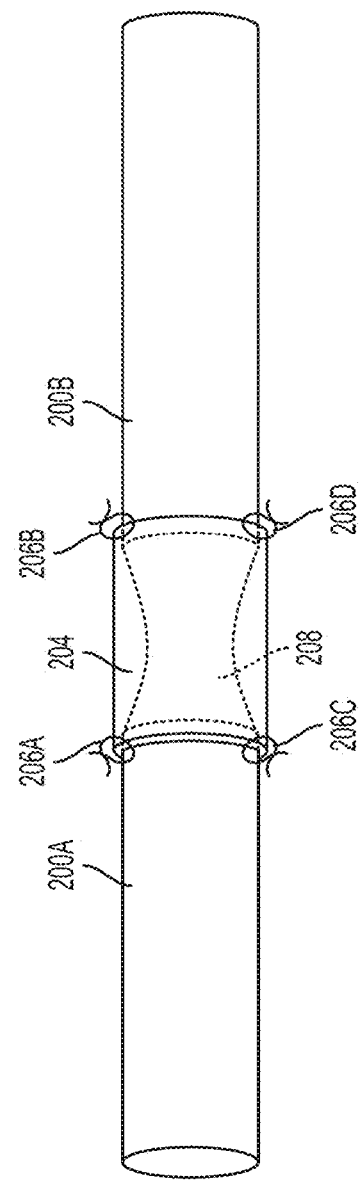

FIG. 3
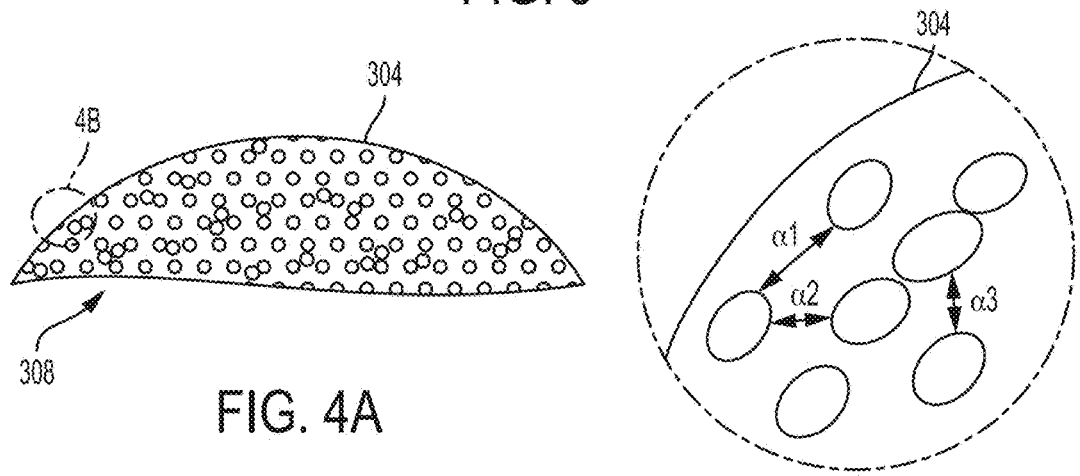
FIG. 4A
FIG. 4B
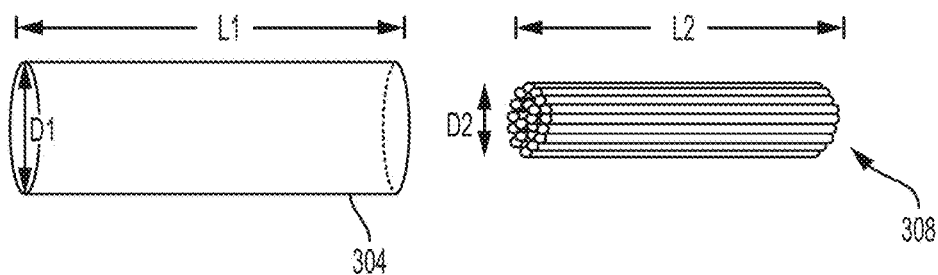
FIG. 5A
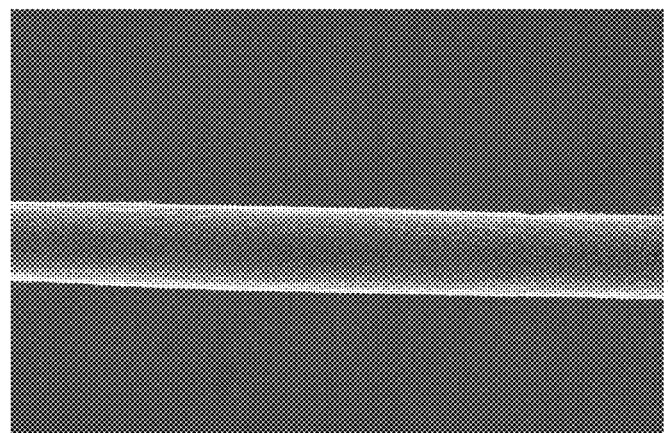
FIG. 5B

Nanofiber forest

Example reactor for growing nanofibers

FABRICATING A CARBON NANOFIBER YARN NERVE SCAFFOLD

TECHNICAL FIELD

The present disclosure relates generally to carbon nanofibers. Specifically, the present disclosure is related to fabricating a carbon nanofiber yarn nerve scaffold.

BACKGROUND

Nerve damage is a difficult medical condition to treat. In particular, upon severing a nerve, regrowth of the nerve can lead to limited restoration of nerve function, persistent nerve pain (sometimes referred to as neuropathy), among other problems. Unlike other types of tissue, merely suturing the severed ends of the nerve together is often inadequate to promote full restoration and healing of the nerve. Some experimental techniques have been developed to improve nerve regeneration. These techniques often include connecting the severed ends of a nerve together by a tube and providing cells (Schwann tissue) that can be used by a body to regenerate nerve cells.

SUMMARY

Example 1 is a method of manufacturing a nerve scaffold, the method comprising: disposing a first strip of adhesive on a roller; wrapping a nanofiber yarn around the roller by rotating the roller, the wrapped nanofiber yarn forming a bundle of aligned segments of the nanofiber yarn on the roller, wherein the nanofiber yarn passes over the first strip of adhesive; separating the bundle of aligned segments of the nanofiber yarn by dividing the strip into two portions; removing the bundle of aligned segments of the nanofiber yarn from the roller; folding the bundle of aligned segments of the nanofiber yarn, wherein the bundle of folded aligned segments of nanofiber yarn includes a first end and a second end opposite to the first end; and configuring the bundle of aligned segments of the nanofiber yarn to be disposed within a tube.

Example 2 includes the subject matter of Example 1, further comprising disposing a second strip of adhesive on the roller, the first strip of adhesive and the second strip of adhesive defining a gap therebetween.

Example 3 includes the subject matter of Example 2, wherein separating the bundle of nanofiber yarn occurs at the gap defined by the first strip of adhesive and the second strip of adhesive.

Example 4 includes the subject matter of any of the preceding Examples, wherein the bundle of aligned segments of the nanofiber yarn includes a midpoint, and wherein the folding comprises folding the bundle of the nanofiber yarn at the midpoint.

Example 5 includes the subject matter of Example 4, wherein the midpoint of the folded bundle is connected to a drawing structure, the drawing structure used to dispose the folded bundle within the tube.

Example 6 includes the subject matter of Example 5, further comprising cutting the first end and second end of the folded bundle of aligned segments of nanofiber yarn.

Example 7 includes the subject matter of Example 6, wherein the cutting of the first end and the second end of the bundle of aligned segments of the nanofiber yarn causes the bundle of aligned segments of nanofiber yarn to expand to fill a cross-section of the tube.

Example 8 includes the subject matter of any of the preceding Examples, wherein the folded bundle of nanofiber yarn includes from 1000 to 8000 aligned segments of the nanofiber yarn.

Example 9 includes the subject matter of any of the preceding Examples, wherein a weight ratio of the folded bundle of the nanofiber yarn to the tube in which the folded bundle is disposed is about 0.65 to about 1.

Example 10 includes the subject matter of any of the preceding Examples, wherein the nanofiber yarn has a diameter of from 5 µm to 30 µm.

Example 11 includes the subject matter of any of the preceding Examples, wherein the nanofiber yarn has a diameter of from 13 µm to 15 µm.

Example 12 includes the subject matter of any of the preceding Examples, wherein the nanofiber yarn is comprised of carbon nanotubes.

Example 13 includes the subject matter of any of the preceding Examples, further comprising further comprising forming the tube by: forming a cylindrical helix comprising a surgical suture material, the cylindrical helix defining an interior; and wrapping a carbon nanofiber sheet around the cylindrical helix on a surface of the helix opposite the interior.

Example 14 includes the subject matter of any of the preceding Examples, wherein a mass of the bundle nanofiber yarn is from 1.5 mass % to 2.5 mass % of a total mass of a nerve scaffold comprising the bundle and the tube in which the bundle is disposed.

Example 15 includes the subject matter of any of the preceding Examples, wherein a mass of the bundle of nanofiber yarn is from 4.5 mass % to 5.5 mass % of a total mass of the bundle and a tube in which the bundle is disposed.

Example 16 includes the subject matter of any of the preceding Examples, wherein a mass of the bundle of nanofiber yarn is from 9.5 mass % to 10.5 mass % of a total mass of the bundle and a tube in which the bundle is disposed.

Example 17 includes the subject matter of any of the preceding Examples, wherein the nanofiber yarn is a false twisted nanofiber yarn.

Example 18 includes the subject matter of any of the preceding Examples, wherein the nanofiber yarn is a single ply false twisted nanofiber yarn.

Example 19 includes the subject matter of any of the preceding Examples, wherein a surface of the nanofiber yarn has an absence of surface topographic features greater than 1 µm above or below a surface of the nanofiber yarn.

Example 20 includes the subject matter of any of the preceding Examples, wherein a surface of the nanofiber yarn has surface topographic features less than 0.1 µm above or below a surface of the nanofiber yarn.

Example 21 includes the subject matter of any of the preceding Examples, wherein the bundle of aligned segments of nanofiber yarn occupies between 1 and 5%, 1 and 10%, 1 and 20%, 1 and 30%, 1 and 40% or 1 and 50% of a volume of a tube in which the bundle is disposed.

Example 22 includes the subject matter of any of the preceding Examples, wherein an average distance between proximate aligned segments of the nanofiber yarn disposed within the tube is from 5 µm to 15 µm.

Example 23 includes the subject matter of any of the preceding Examples, wherein an average distance between proximate aligned segments of the nanofiber yarn disposed within a tube is from 5 µm to 12 µm.

Example 24 is a carbon nanofiber nerve scaffold comprising a cylindrical helix comprising a surgical suture material, the cylindrical helix defining an interior; a bundle of aligned carbon nanofiber yarns within the interior of the cylindrical helix; and a carbon nanofiber sheet around the cylindrical helix on a side of the cylindrical helix opposite the interior.

Example 25 includes the subject matter of Example 24, wherein the aligned segments of the bundle are spaced from 5 μm to 15 μm from one another.

Example 26 includes the subject matter of Examples 24-25, wherein the carbon nanofiber sheet includes a bioresorbable polymer infiltrant.

Example 27 includes the subject matter of Examples 24-26, wherein the cylindrical helix comprises a first helix wrapped in a first direction and a second helix wrapped in a second direction opposite the first helix.

Example 28 includes the subject matter of Examples 24-27, wherein the cylindrical helix is a crocheted cylindrical helix.

Example 29 includes the subject matter of Examples 24-27, wherein the cylindrical helix is a knitted cylindrical helix.

BRIEF DESCRIPTION OF THE DRAWINGS

FIG. 1 is a schematic illustration of a severed nerve fiber connected together with a tubular nerve scaffold.

FIG. 2 is a schematic illustration of a severed nerve fiber connected together with tubular nerve scaffold, in which nerve fiber has regrown between the two severed nerve portions.

FIG. 3 illustrates a carbon nanofiber nerve scaffold, in an example of the present disclosure.

FIG. 4A illustrates an enlarged view of a portion of the carbon nanofiber nerve scaffold depicted in FIG. 3, in an example of the present disclosure.

FIG. 4B illustrates an enlarged view of a portion of the carbon nanofiber nerve scaffold depicted in FIG. 4A, in an example of the present disclosure.

FIG. 5A is an exploded view of the carbon nanofiber nerve scaffold depicted in FIG. 3, in an example of the present disclosure.

FIG. 5B is the scanning electron microscope (SEM) image of a singly ply, false twisted nanofiber used in a carbon nanofiber nerve scaffold, in an example of the present disclosure.

Figure 6:
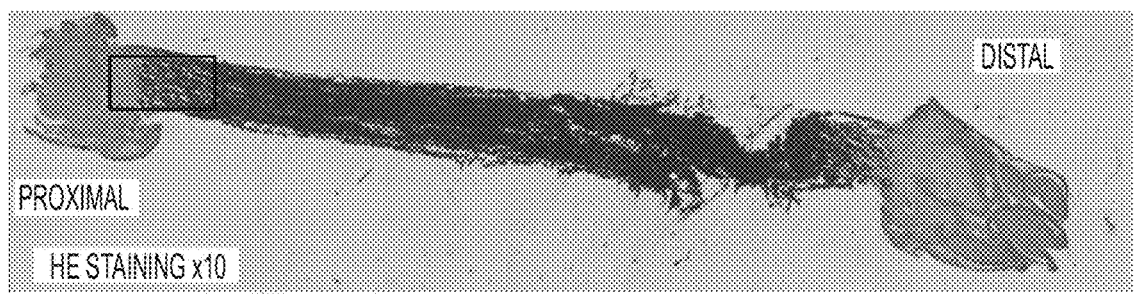
FIGS. 6 and 7 are optical microscope images of a histological specimen of a carbon nanofiber nerve scaffold having a 65% mass of nanofibers relative to the entire mass of the nerve scaffold, in an example of the present disclosure.

The figures depict various embodiments of the present disclosure for purposes of illustration only. Numerous variations, configurations, and other embodiments will be apparent from the following detailed discussion. Furthermore, as will be appreciated, the figures are not necessarily drawn to scale or intended to limit the described embodiments to the specific configurations shown. For instance, while some figures generally indicate straight lines, right angles, and smooth surfaces, an actual implementation of the disclosed techniques may have less than perfect straight lines and right angles, and some features may have surface topography or otherwise be non-smooth, given real-world limitations of fabrication processes. In short, the figures are provided merely to show example structures.

DETAILED DESCRIPTION

Overview

Neurotmesis is a nerve injury in which the nerve and its sheath are severed. This causes loss of sensation and paralysis in the muscle that the nerve controls. Generally, the nerve does not recover without medical intervention. Symptoms of neurotmesis can be treated with opioids and anti-inflammatory drugs, while restoration of the nerve and its associated function can be assisted through surgery. Surgical methods to facilitate recovery of the nerve include sewing the nerve endings together, implanting a nerve graft, or implanting a "nerve scaffold."

Sewing the ends of the nerve together can have drawbacks. For example, suturing the nerve ends together causes tension within the sutured nerve. This tension can inhibit regrowth, increase the possibility of scarring, and may not significantly improve nerve function. Similarly, using a nerve graft can also have drawbacks. For example, upon removing a portion of nerve from a living donor to provide to the recipient, the donor will experience sensory loss at locations in the body previously served by the removed nerve.

The use of a hollow nerve scaffold to facilitate regrowth of a severed nerve is a subject of continuing research. A scaffold is a biocompatible tube that is sutured to the ends of the nerve. In some examples, the scaffold has multiple, small channels that act as a guide for the re-growing nerve fibers, while in other examples a scaffold is merely a hollow tube defining a single interior chamber. Regardless of the interior configuration, the goal of a scaffold is to create an environment facilitating regrowth of the nerve fibers to aid recovery of muscle function.

The latter scenario of a hollow tube nerve scaffold is schematically illustrated in FIG. 1. In this example, nerve segments 100A and 100B have been severed from one another. A hollow tube nerve scaffold 104 is disposed over the confronting ends of the severed nerve segments 100A and 100B to facilitate nerve fiber regrowth.

One drawback of some types of nerve scaffolds, such as the example nerve scaffold 104, is that the regrown nerve fiber experiences a tensile force during regrowth. This can lead to a nerve fiber that is constricted in locations, which in turn can cause reduced nerve function, nerve pain, or other undesirable outcomes. For example, as shown in FIG. 2, nerve segments 200A and 200B have been severed and reconnected via hollow tube nerve scaffold 204. The nerve scaffold 204 is attached to the nerve segments 200A and 200B via sutures 206A, 206B, 206C, and 206D. As shown, the regenerated nerve fiber 208 has an hourglass shape with the constriction disposed between the confronting faces of the nerve segments 200A and 200B. This constriction within the regenerated nerve fiber 208 can cause some or all of the undesirable outcomes identified above.

Thus, in accordance with some examples described herein, the present disclosure describes nerve scaffolds that include a tubular outer housing fabricated from a biocompatible material, within which are disposed a plurality of carbon nanofiber yarns. The carbon nanofiber yarns, which can be separated from adjacent yarns by distances roughly corresponding to an average nerve fiber diameter, provide surfaces on which nerve fibers can regrow. Because the proximate carbon nanofiber yarns can support individual nerve fibers (in part due to this convenient dimensional separation between nanofiber yarns) the likelihood of the nerve fibers being tensile stressed during regrowth is reduced. In some examples of the present disclosure, the magnitude of a tensile stress on the regenerated nerve fibers is reduced relative to nerve fibers regenerated using nerve scaffolds that do not include carbon nanofiber yarns. For at least these reasons, the likelihood of undesirable outcomes of nerve pain or reduced nerve function are reduced when using embodiments of the present disclosure as a nerve scaffold.

Example Nerve Scaffold

As indicated above, in some examples of the present disclosure nerve scaffolds include a plurality of yarns fabricated from carbon nanofibers and/or carbon nanotubes. The present disclosure will refer primarily to carbon nanofibers but it will be appreciated that carbon nanotubes share many of the same advantageous features and are included within the generic term of "carbon nanofibers." Carbon nanofibers, and more specifically carbon nanofiber yarns, are beneficial to use as a component of an example nerve scaffold as described herein because the carbon nanofiber yarns are electrically conductive and biocompatible. For example, when a carbon nanofiber is used as a component of a scaffold (e.g., within the tubular component described above), pathways between adjacent carbon nanofiber yarns can be defined. Nerve fibers can grow (also referred to equivalently as "regeneration") within these pathways. The carbon nanofiber yarns can also provide electrically conductive pathways from one segment of a severed nerve to another segment of the severed nerve. The presence of an electrically conductive pathway can improve nerve growth and it can also improve nerve function beyond what may generally be expected for a regenerated nerve. In some examples, it is believed that the use of carbon nanofiber yarns within a nerve scaffold can cause nerve function of a regenerated nerve to approach that of the same nerve prior to the severing injury. In some examples, carbon nanofibers, and in particular single ply, false twisted carbon nanofiber yarns can provide a topographically smooth and nanoporous support surface on which nerve fibers can grow, facilitating low tensile stress nerve fiber regrowth.

One example of a nerve scaffold of the present disclosure is schematically shown in FIG. 3. The nerve scaffold 300 includes a tube 304 and a plurality of nanofiber yarns 308. The benefits of the nerve scaffold 300 include providing gaps or pathways between, and defined by, the nanofiber yarns of the plurality. These gaps are configured and dimensioned to encourage nerve growth and can provide an electrical connection between the segments of the severed nerve.

The tube 304 can perform any of a number of functions. In some examples, the tube 304 separates the region in which nerve fibers can regrow from the surrounding environment. This can help protect the regrowing nerve fibers from physical damage or other perturbations that may otherwise reduce the growth rate or the continuity of the regrowing nerve. The tube 304 also defines a space in which carbon nanofiber yarns can be disposed and configured so as to have a density and an arrangement that facilitates nerve fiber regrowth, as described herein.

The tube 304 can be fabricated from biocompatible and/or bioresorbable materials. Examples of these materials include silicone, which has the added advantage of being compliant rather than rigid. This compliance facilitates attachment of the ends of the tube 304 to proximate nerve segments via suturing (as illustrated in FIG. 2). Other examples of biocompatible materials that can be used for the tube 304 include, but are not limited to poly(methyl methacrylate), poly(tetrafluoroethylene), polyethylene, polyglycolide, polycaprolactam, poly (lactic-co-glycolic acid), poly lactic acid, poly (glycerol sebacate), polysialic acid, polyethylene glycol, polyurethane, collagen, chitosan, silk, and alginate, among others. In another set of embodiments, the tube can be made of carbon, such as carbon nanotubes. In some embodiments, the tube 304 can be made of biological materials including blood vessels and skeletal muscles. In specific embodiments, both a carbon nanotube tube and carbon nanotube yarns can be used together to promote nerve regeneration.

As described above, the plurality of nanofiber yarns 308 can include true twisted multi-ply and single ply nanofiber yarns, untwisted multi-ply and single ply nanofiber yarns, and false twisted multi-ply and single ply nanofiber yarns. The plurality of nanofiber yarns 308 can be disposed within the tube 304 to define a structure of inter-fiber spaces into which regenerated nerve fibers can grow. The nanofiber yarns provide a smooth and nanoporous surface onto which nerve fibers can grow and can also provide mechanical support for the regrowing nerve fiber. With this mechanical support, the regrowing nerve fibers and the regenerating nerve as a whole are less likely to experience tensile or compressive stresses that can cause neuropathic pain or negatively impact nerve fiber growth.

The plurality of nanofiber yarns 308 (the fabrication of which is described below in the context of FIGS. 12-15) can be disposed within the tube 304, as shown in FIG. 3. While the nanofiber yarns in FIG. 3 are shown as being parallel to one another and distributed evenly within the tube 304, it will be appreciated that this is for convenience of illustration only. Rather, nanofiber yarns are assembled into the plurality of nanofiber yarns 308 so as to occupy a portion of the volume defined by the tube 304 and be substantially aligned with one another, but not necessarily exactly parallel to one another. It is sufficient in many embodiments for this general alignment of nanofiber yarns within the plurality of nanofiber yarns 308 to define pathways (also referred to as gaps and/or spaces) between the nanofiber yarns that roughly correspond to a cross-sectional diameter of the nerve fiber. This is generally from 5 μm to 10 μm in diameter, and in some examples from 8 μm to 10 μm. Even in circumstances in which nanofiber yarns cross one another or are misaligned, having spaces that are at least partially continuous along a length of the tube 304 (i.e., greater than 10% or greater than 20% along a length of the tube 304) and within the range of 5 μm to 10 μm in diameter is sufficient to facilitate nerve regeneration in a way that minimizes the tensile forces described above.

FIGS. 4A and 4B illustrate this beneficial configuration of nanofiber yarns within a tube to form an example of the carbon nanofiber yarn nerve scaffold 300 of the present disclosure. Concurrent reference to both FIGS. 4A and 4B will facilitate explanation. As shown in these figures, cross-sectional diameters of the nanofiber yarns of the plurality of nanofiber yarns 308 are oriented similarly (within)+/−10° to the cross-section of the tube 304. Similarly, a length of the tube 304 and the length of the nanofiber yarns of the plurality of nanofiber yarns 308 are aligned in generally the same direction (allowing for variations in orientation at the micron and/or nanometer scale for nanofiber yarns of the plurality).

One result of this orientation of nanofiber yarns is, as indicated above, definition of spaces between the nanofiber yarns into which nerve fibers can grow when regenerating. Examples of spaces defined by adjacent nanofibers are illustrated in enlarged view FIG. 4B. As shown, proximate nanofiber yarns of the plurality are separated from one another by distances denoted as $\alpha 1$, $\alpha 2$, and $\alpha 3$. To promote nerve growth, the widths $\alpha 1$, $\alpha 2$, and $\alpha 3$ of the spaces between at least some of the nanofiber yarns can be within any of the following ranges: from 5 μm to 10 μm; from 5 μm to 12 μm; from 5 μm to 8 μm; from 5 μm to 10 μm; and from 8 μm to 10 μm. Because nerve fibers are generally approximately 8 μm in diameter (+/−10%), spaces between nanofiber yarns having the widths $\alpha 1$, $\alpha 2$, and $\alpha 3$ are thus dimensioned and configured to support nerve fiber regrowth. Widths greater than the previously recited ranges of $\alpha 1$, $\alpha 2$, and $\alpha 3$ can, in some examples, provide an adequate support for the regrowing nerve fibers so as to reduce the tensile stress on the nerve fibers. Therefore, in some cases, the spaces between nanofiber yarns can be less than 20, less than 15 μm, less than 12 μm, less than 10 μm, or less than 8 μm. Widths narrower than the previously recited ranges of $\alpha 1$, $\alpha 2$, and $\alpha 3$ can, in some examples, either prevent a nerve fiber from growing through the plurality of nanofiber yarns or can allow a nerve fiber to grow in a physically constrained environment in which a compressive force exists between the nerve fiber and the adjacent nanofiber yarns in contact with the nerve fiber. This can lead to limited nerve function and/or neuropathic pain. In some cases, the spaces between nanofiber yarns can be greater than 1 μm, greater than 2 μm, greater than 3 μm, greater than 5 μm, or greater than 7 μm.

In some examples, the individual nanofiber yarns of the plurality of nanofiber yarns 308 are false twisted, single ply, nanofiber yarns. Techniques by which nanofiber yarns can be false twisted are described in U.S. patent application Ser. No. 15/844,756, which is incorporated herein by reference in its and entirety. While not wishing to be bound by theory, it is believed that in some cases a relatively smooth and nanoporous surface of a single ply nanofiber yarn, particularly a false twisted nanofiber yarn provides a surface on which nerve fiber regrowth is encouraged. This smooth surface includes a surface topography on the nanofiber yarn lacking features that are more than 100 nm above or below a surface of the yarn as a whole.

FIG. 5A illustrates an exploded view of the nerve scaffold 300 that includes the tube 304 and the plurality of nanofiber yarns 308. As shown, the tube 304 has a length L1 and an inner diameter D1. The length L1 is dimensioned according, in part, to a size of the gap between confronting faces of a severed nerve. In some examples the length L1 can be within any of the following ranges: from 1 mm to 2 cm; from 1 mm to 1 cm; from 1 mm to 0.5 mm; from 1 cm to 2 cm; from 1.5 cm to 2 cm; from 5 mm to 1.5 cm. The inner diameter D1 is dimensioned so that the tube 304 can be disposed over severed ends of a nerve and sutured or otherwise connected thereto, as illustrated in FIG. 2. In some examples the inner diameter D1 can be within any of the following ranges: from 1 mm to 40 mm; from 1 mm to 5 mm; from 3 mm to 10 mm; from 1 mm to 15 mm; from 10 mm to 30 mm; from 15 mm to 40 mm.

As shown, the plurality of nanofiber yarns 308 has a length L2 and an outer diameter D2. The length L2 is dimensioned according to, in part, the size of the gap between confronting faces of a severed nerve and the length L1 of the tube 304. In some examples it is preferable that the length L2 be equal to L1 or less than the length L1 so that enough material of the tube 304 can overlap the ends of nerve segments to be sutured thereto. In some examples, the length L2 is sufficient to contact confronting faces of nerve segments (in other words, to bridge the severed nerve) or be within 5 μm of each of the severed nerve segment faces. In some examples, the length L2 can be within any of the following ranges: from 1 mm to 2 cm; from 1 mm to 1 cm; from 1 mm to 0.5 mm; from 1 cm to 2 cm; from 1.5 cm to 2 cm; from 5 mm to 1.5 cm.

The outer diameter D2 of the plurality of nanofiber yarns 308 is dimensioned and configured so that the plurality of nanofiber yarns 308 can be disposed within the tube 304. In some examples, the outer diameter D2 is from 2% to 10% less than the inner diameter D1 of the tube 304. When the outer diameter D2 of the plurality of nanofiber yarns 308 is dimensioned to be slightly smaller than the inner diameter D1 of the tube 304, the plurality of nanofiber yarns 308 is small enough to be inserted into the space defined by the tube 304 but large enough to form an interference fit with the adjacent inner surface of the tube 304. This interference fit enables the plurality of nanofiber yarns 308 to be firmly lodged within the tube 304 and not unintentionally slide out. In some cases, the bundle of nanofiber yarns can be compressed to a smaller diameter to more easily pass into the tube. Once in the tube, the bundle can be allowed to expand to the full inner diameter of the tube. Furthermore, thus dimensioned, the plurality of nanofiber yarns 308 can be distributed across to an entire cross-section of the tube 304 that is coincident with the inner diameter D1 and perpendicular to the length L1. Having nanofiber yarns of the plurality 308 distributed throughout both the length and the cross-sectional diameter of the tube 304 provides many interstitial spaces into which nerve fibers can grow.

In some embodiments, the interstitial spaces between proximate nanofiber yarns can include one or more polymer matrices to support nerve fiber growth. In some examples, the polymer matrices can be one or more of collagen, gelatin, or fibrin. In some other examples, the polymer matrices can be one or more of the glycosaminoglycans.

In some embodiments, the interstitial spaces between proximate nanofiber yarns can also include one or more proteins or growth factors. In some examples, the protein or the growth factors can be at least one of a vascular endothelial growth factor (VEGF), a nerve growth factor (NGF), a hepatocyte growth factor (HGF), or a fibrin matrix gel. In one specific example, the interstitial spaces include a nerve growth factor.

In yet another embodiment, the interstitial spaces between proximate nanofiber yarns can include one or more polymer matrices in combination with one or more proteins. In a specific example, the interstitial spaces include collagen in combination with nerve growth factor.

In some examples, the proper spacing between adjacent nanofiber yarns of the plurality of nanofiber yarns 308, indicated above, can be measured indirectly as the percentage of carbon nanofiber yarn mass relative to the total mass of nerve scaffold (i.e. the mass of the tube plus the plurality of carbon nanofiber yarns). This percentage of carbon nanofiber yarn mass relative to the total carbon nanofiber nerve scaffold mass is optionally described herein as "packing density" for brevity. In some examples, nerve fiber growth within the carbon nanofiber yarn nerve scaffold of the present disclosure was found to be satisfactory (in terms of nerve signal transmission time and regrown nerve fiber morphology, as described below in the context of FIGS. 6, 7, 9A-11C) for packing densities in any of the following ranges: less than 2%; from 2% to 5%, from 2% to 10%. The density of the yarns in the tube can also be measured on a cross-sectional area basis. For example, the ratio of the cumulative cross sections of the yarns in bundle 308 to the cross sectional area of the tube (inner diameter) can be greater than 1%, greater than 5%, greater than 10%, greater than 20%, greater than 30%, greater than 40%, greater than 50%, less than 75%, less than 65%, less than 50%, less than 40%, less than 30% less than 20%, less than 10%, less than 5% or less than 3%.

While packing density is a macroscopic measurement, it has been found experimentally that packing density can predict an average diameter of spaces between individual nanofibers of the plurality 308. This in turn enables the plurality of nanofiber yarns 308 to be easily measured so as to be configured to facilitate nerve fiber growth. For example, packing densities of single ply false-twisted nanofiber yarns in the range of from 2% to 10%, as described below in more detail, have been found to have interfiber spaces that are between 8 µm and 10 µm in diameter. As described above, many nerve fibers cross-sectional diameters are in this range. Thus, the carbon nanofiber yarn nerve scaffold of the present disclosure that has a nanofiber yarn packing density of from 2% to 10% is configured to facilitate regrowth of many different types of nerve fibers in a way that reduces tensile stress on the nerve fibers relative to an empty tube scaffold. Also, the carbon nanofiber yarn nerve scaffold of the present disclosure reduces compressive stress on the nerve fibers from gaps that would have smaller than cross-sectional diameters than the nerve fibers.

In other examples, packing densities can be within any of the following ranges: from 1% to 40%; from 2% to 35%; from 2% to 65%. However, it will be appreciated that packing densities that are too high (for example, greater than 65%) correspond to spaces between adjacent nanofiber yarns that are too small (e.g., less than 5 µm, less than 2 µm) for nerve fibers to grow into. Analogously, low packing densities (in some examples, found to be less than 5%) correspond to spaces between adjacent nanofiber yarns that are too large to provide a structure onto which nerve fibers are physically supported when regrowing. This can lead to the tensile stress on the fibers, as described above.

In some examples, it has been found that, depending on an outer diameter of the individual nanofiber yarns themselves, described below in the context of FIG. 5B, between 1000 and 8000 single ply, false twisted nanofiber yarns can be configured to form the packing densities described above for a tube 304 having a cross-sectional diameter of 15 mm.

It has also been experimentally observed that the more uniform and aligned the carbon nanofiber yarns, the more likely nerve growth will be encouraged. Experimental results are presented below.

FIG. 5B illustrates the scanning electron microscope (SEM) image of a single ply, false twisted nanofiber yarn of the present disclosure. As indicated above, false twisting techniques are described in U.S. patent application Ser. No. 15/844,756, which is incorporated by reference herein in its entirety. In some examples, a single ply, false twisted nanofiber yarn used in carbon nanofiber nerve scaffolds of the present disclosure such as the one illustrated in FIG. 5B, can have a cross-sectional diameter (taken perpendicular to a longitudinal axis of the yarn which in this case indicated by the double-headed arrow in FIG. 5A) within any of the following ranges: from 5 µm to 40 µm; from 5 µm to 30 µm; from 5 µm to 20 µm; from 10 µm to 30 µm; from 50 µm to 40 µm; from 25 µm to 35 µm, less than 40 µm, less than 30 µm, less than 20 µm, greater than 5 µm, greater than 10 µm or greater than 20 µm. In the specific example of the nanofiber yarn shown in FIG. 5B, the cross-sectional diameter is approximately 15 µm. Furthermore, as indicated above, one benefits of embodiments of the present disclosure is that the nanofiber yarns provide a smooth surface on which nerve fibers can grow. The nanofiber yarn depicted in FIG. 5B is such a yarn, having surface topography features that are less than 1 µm (and in some examples less than 0.1 µm) above or below an average location of the surface of the yarn (wherein average location is measured from an outer circumference of the yarn taken over a length of the yarn and calculated from a statistically significant sampling).

Experimental Results

Figure 7:
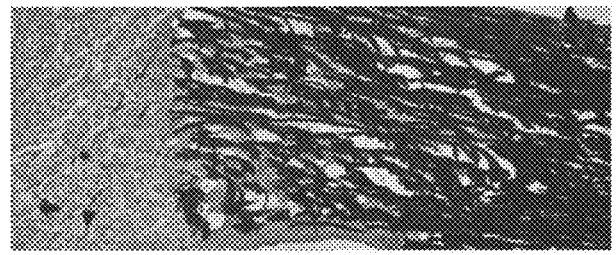

FIGS. 6 to 11C depict various experimental examples of the present disclosure. FIGS. 6 to 8C illustrate various embodiments that can act as references for the embodiments depicted in FIGS. 9 to 11C. For example, FIG. 6 illustrates a histological cross-section of a severed nerve fiber. In this example, regeneration was attempted with a nerve scaffold of the present disclosure having a packing density of carbon nanofiber yarns (single ply, false twisted) of 65%. The yarns (or aligned segments of a yarn) were 14.5 µm in diameter. Approximately 8000 yarn segments were in the bundle. In the cross-section shown in FIG. 6, taken at a magnification of 10×, it can be seen that nerve fiber regrowth from the distal and proximal ends into the intervening (darker) carbon nanofiber yarns is limited. In fact, as shown in FIG. 7, which is a magnification of the boxed region of FIG. 6 at 400×. The regeneration of nerve fibers into the plurality of nanofiber yarns with the packing density of greater than 65% does not extend far from the severed proximal nerve surface. Nor do the regenerating nerve fibers form a continuous fiber from the proximal and to the distal end, thus failing to reestablish neurological connection between the proximal and distal ends of the severed nerve. FIGS. 6 and 7 illustrate the importance of selecting a nerve scaffold of the present disclosure with an appropriate packing density of carbon nanofiber yarns: namely, one that is dense enough to support nerve fibers during the regrowth but not so dense to inhibit regrowth that can reconnect the ends of the severed nerve.

Figure 8A:
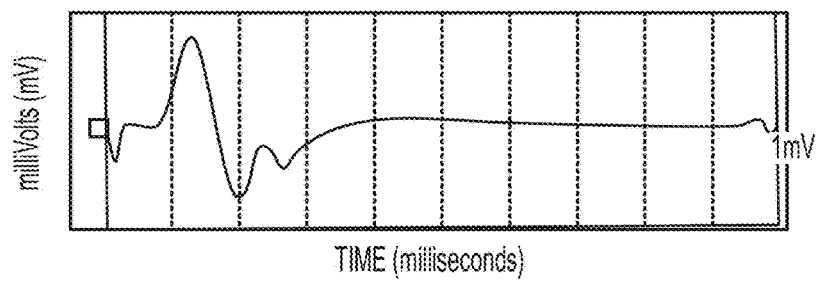
FIG. 8A is an electromyogram of a healthy nerve used as a control sample for comparison to nerves regenerated using carbon nanofiber nerve scaffolds of the present disclosure.
Figure 8B:
FIG. 8B is an optical image of a histological cross-section of a healthy nerve used as a control sample for comparison to nerves regenerated using carbon nanofiber nerve scaffolds of the present disclosure.
Figure 8C:
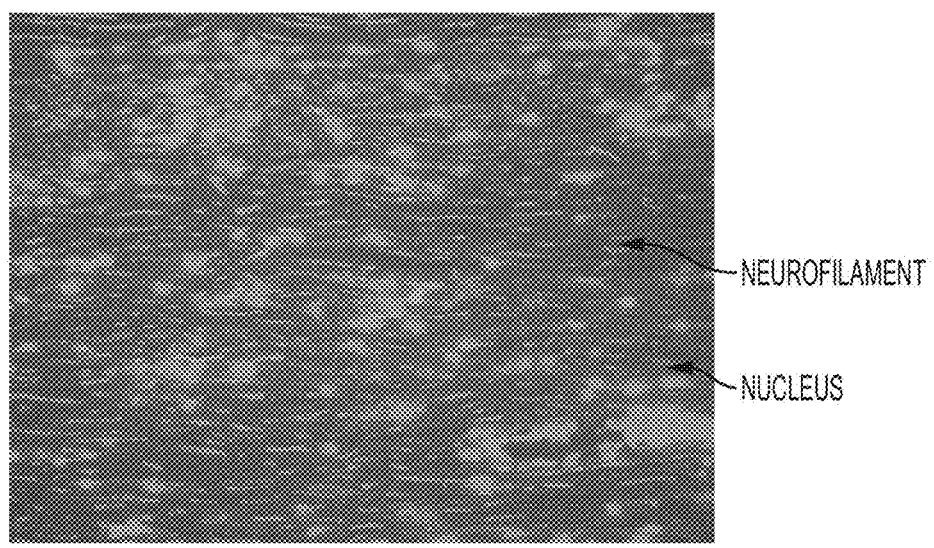
FIG. 8C is an enlarged view of a portion of the histological cross-section in FIG. 8B showing neural filaments and nerve cell nuclei.

FIGS. 8A-8C illustrate another point of reference for embodiments described herein, in which the healthy nerve that has not been severed nor regenerated using a nerve scaffold of any kind. FIG. 8A is an electromyogram of this healthy nerve. Two measurements are generally taken using electromyography: the distal latency and the amplitude. Together, these characterize the speed of propagation of an electrical signal through the nerve in response to stimuli and the strength of that signal, respectively. The graph depicted in FIG. 8A corresponds to the healthy nerve, a cross-section of which is depicted in FIGS. 8B and 8C. A summary of the electromyography results from three separate healthy rat sciatic nerves that have been severed and then sutured to a nerve scaffold are summarized in Table 1, below.

The image of FIG. 8B was taken at an optical magnification of 40× and the image of FIG. 8C was taken at an optical magnification of greater than 40×. FIG. 8C is provided merely to illustrate the continuity of nerve fiber filaments with cell nuclei.

Figure 9A:
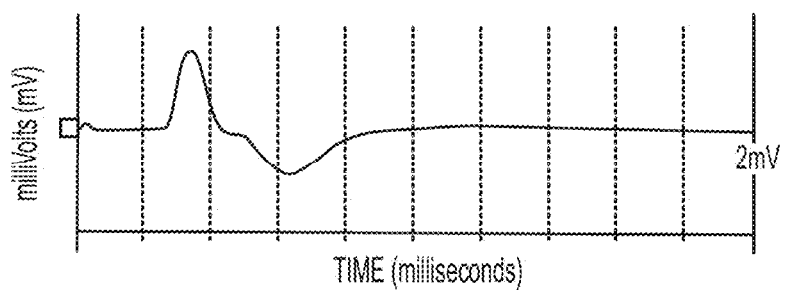
FIG. 9A is an electromyogram of a severed nerve fiber regenerated using a carbon nanofiber nerve scaffold with 2 mass % nanofiber yarns relative to the entire mass of nerve scaffold, in an example of the present disclosure.
Figure 9B:
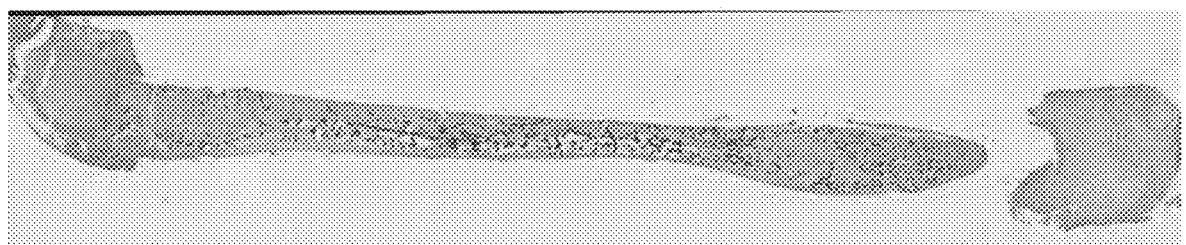
FIG. 9B is an optical image of a histological cross-section of the nerve fiber regenerated using a carbon nanofiber scaffold with 2 mass % nanofiber yarns relative to the entire mass of nerve scaffold, as electrically analyzed in FIG. 9A, in an example of the present disclosure.
Figure 9C:
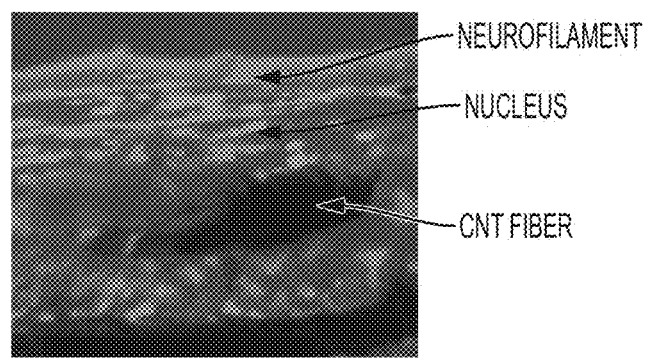
FIG. 9C is an enlarged view of a portion of the histological cross-section in FIG. 9B showing neural filaments and nerve cell nuclei in contact with carbon nanofiber yarns of the scaffold, in an example of the present disclosure.

FIGS. 9A, 9B, and 9C correspond to a severed nerve that has regenerated using a nerve scaffold of the present disclosure with a 2% packing density. FIG. 9A is an example electromyogram of one example of this embodiment, FIG. 9B is a histological cross-section taken at an optical magnification of 40×, and FIG. 9C is a magnified image of a portion of the cross-section of FIG. 9B taken at an optical magnification of greater than 40×.

The electromyogram corresponding to FIG. 9A has a distal latency and amplitude that are summarized below in table 1. As can be seen, particularly in contrast to FIG. 6 and FIG. 7, FIG. 9B and FIG. 9C show the regenerated nerve fibers (which include neurofilament and nuclei of nerve cells) connecting both ends of the severed nerve. The gap in the nerve between the rightmost portion of the nerve and the center portion of the nerve is an artifact of the cross-section and process and is not indicative of a discontinuity in the regenerated nerve. Furthermore, as can be seen in the magnified view of FIG. 9C, neurofilaments and nerve cell nuclei are in intimate contact with carbon nanotube yarns, as described above. The presence of both neurofilaments and nuclei in close proximity to carbon nanofibers are suggestive of a functioning regenerated nerve. This is in contrast to regenerated tissue that is primarily scar tissue, which lacks the nuclei and nerve fibers of a functioning nerve. Nerve function in the regenerated nerve is also indicated by the electromyography results, discussed below in the context of table 1. The results of this sample, including the electromyography results discussed below, indicate the benefits to nerve regeneration and the restoration of nerve function that are provided by a nerve scaffold of the present disclosure.

Figure 10A:
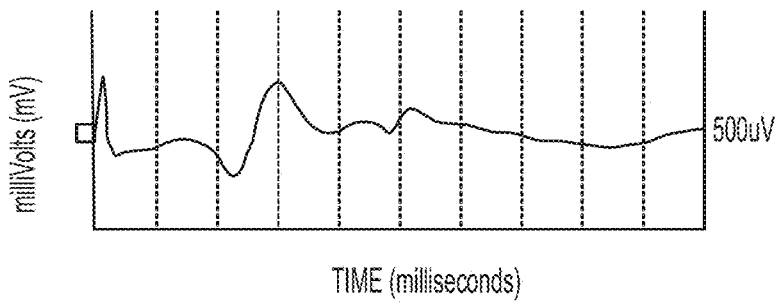
FIG. 10A is an electromyogram of a severed nerve fiber regenerated using a carbon nanofiber nerve scaffold with 5 mass % nanofiber yarns relative to the entire mass of nerve scaffold, in an example of the present disclosure.
Figure 10B:
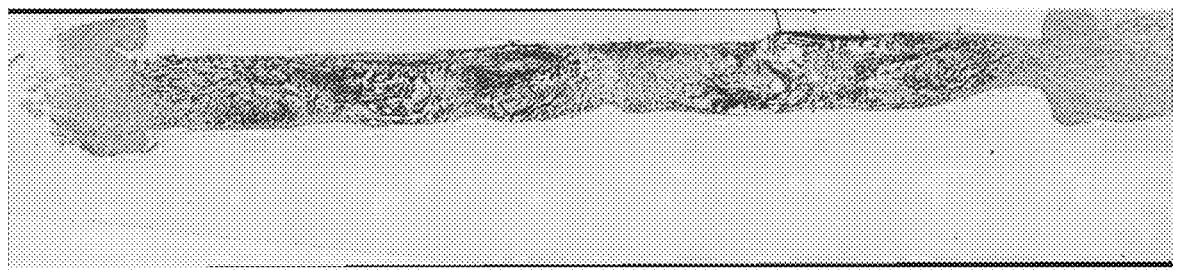
FIG. 10B is an optical image of a histological cross-section of the nerve fiber regenerated using a carbon nanofiber nerve scaffold with 5 mass % nanofiber yarns, as electrically analyzed in FIG. 10A, in an example of the present disclosure.

FIGS. 10A and 10B correspond to a severed nerve that has regenerated using a nerve scaffold of the present disclosure with a 5% packing density. FIG. 10A is an example electromyogram of the embodiment shown. FIG. 10B is a histological cross-section taken at an optical magnification of 40×. As with the example depicted in FIGS. 9A-9C, the electromyography data and the image itself illustrate neurofilament and nerve cell nuclei regrowth in intimate contact with the carbon nanofiber yarns so as to reestablish nerve function between the previously severed ends of the nerve.

Figure 11A:
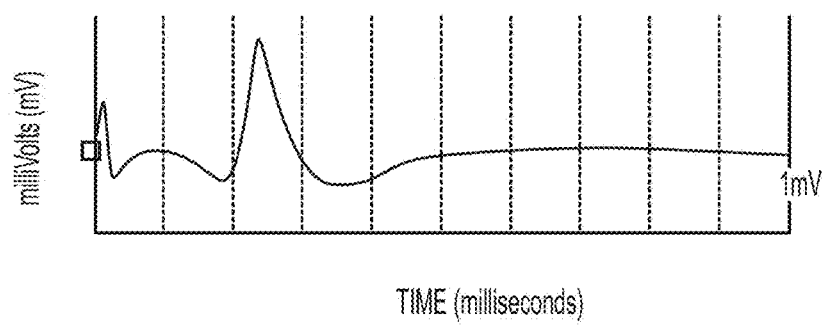
FIG. 11A is an electromyogram of a severed nerve fiber regenerated using a carbon nanofiber nerve scaffold with 10 mass % nanofiber yarns relative to the entire mass of nerve scaffold, in an example of the present disclosure.
Figure 11B:
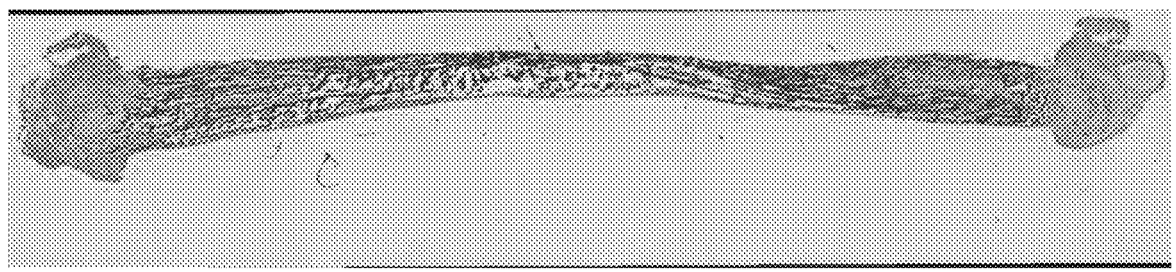
FIG. 11B is an optical image of a histological cross-section of the nerve fiber regenerated using a carbon nanofiber nerve scaffold with 10 mass % nanofiber yarns, as electrically analyzed in FIG. 11A, in an example of the present disclosure.
Figure 11C:
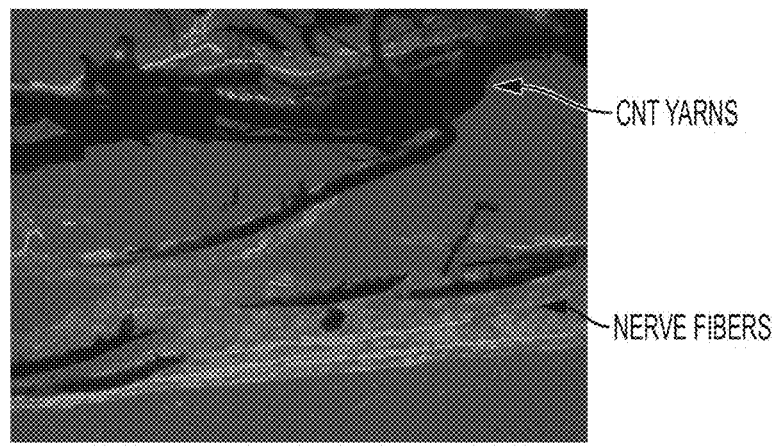
FIG. 11C is an enlarged view of a portion of the histological cross-section in FIG. 11B showing neural filaments and nerve cell nuclei in contact with carbon nanofiber yarns, in an example of the present disclosure.

FIGS. 11A, 11B, and 11C correspond to a severed nerve that has been regenerated using a nerve scaffold of the present disclosure with a 10% packing density. FIG. 11A is an example electromyogram of one example of this embodiment, FIG. 11B is a histological cross-section taken at an optical magnification of 40×, and FIG. 11C is an image of a portion of the cross-section of FIG. 11B taken at an optical magnification of 40×.

As with the preceding examples, the example depicted in FIGS. 11A-11C illustrates nerve fibers in intimate contact with carbon nanotube yarns and a continuous nerve pathway between the previously severed nerve ends.

The electromyography data for the preceding experimental examples are summarized below in table 1. As can be seen, each of the 2%, 5%, and 10% packing density embodiments of the present disclosure produced distal latencies and amplitudes within a factor of 2.5 of the healthy nerve acting as a reference. In fact, one of the three samples tested for the 2% packing density example embodiment produced a distal latency and an amplitude that were on par with the healthy nerve.

TABLE 1

| Sample (FIG. Nos.) | Sample Size | Average (Range) Distal Latency (milliseconds) | Amplitude (Range) (milliVolts) |
|---|---|---|---|
| Healthy (8A-8C) | 5 | 2.23 (1.42-2.95) | 7.16 (4.35-9.31) |
| 2% Packing Density (9A-9C) | 3 | 4.59 (2.64-6.2) | 5.59 (2.34-7.62) |
| 5% Packing Density (10A, 10B) | 3 | 5.71 (4.58-7.35) | 3.26 (2.32-3.76) |
| 10% Packing Density (11A-11C) | 3 | 5.38 (3.97-7.85) | 4.44 (2.61-6.66) |

Methodology

Figure 12:
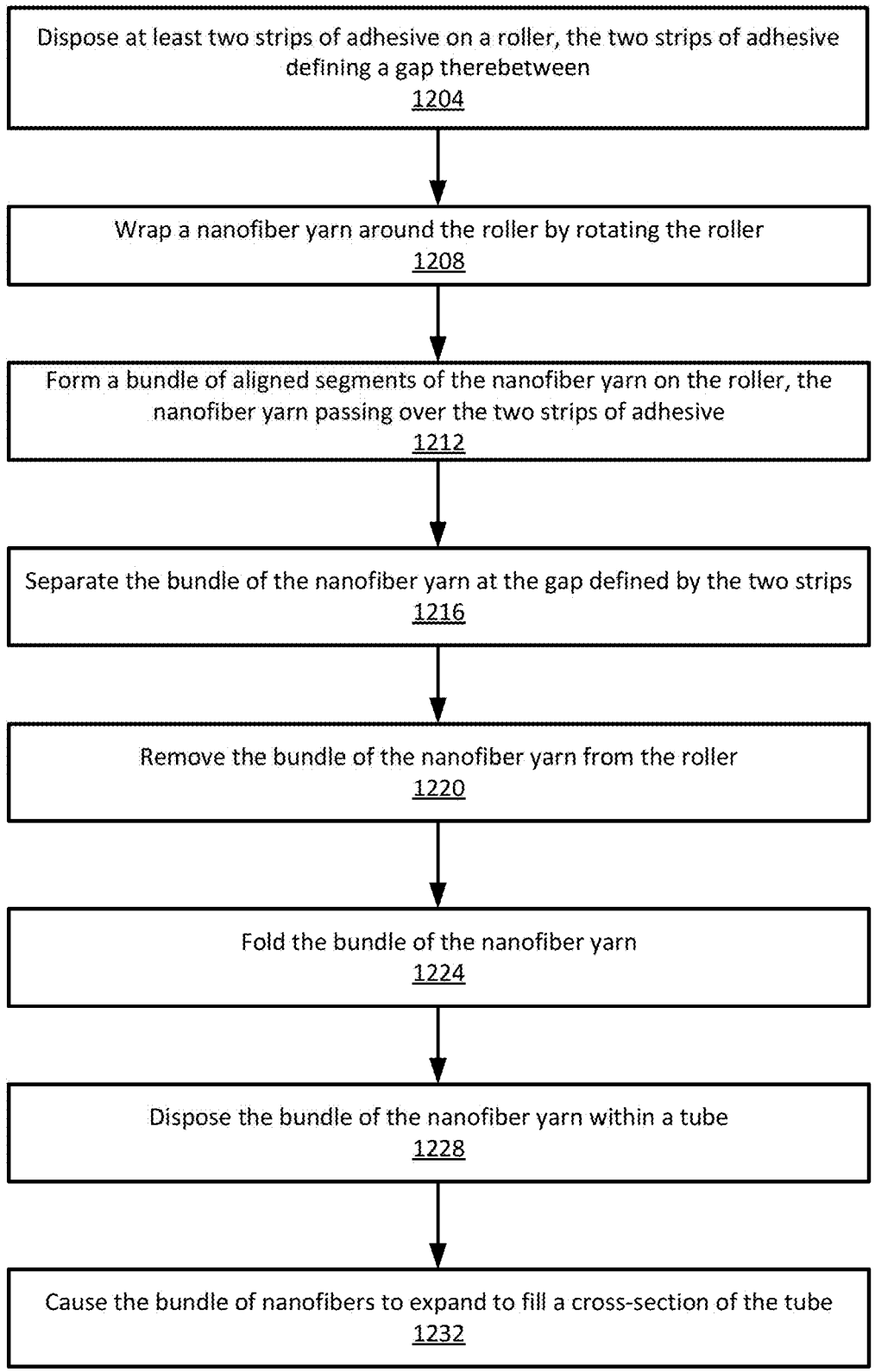
FIG. 12 is a method flow diagram of an example method for manufacturing a nerve scaffold, in embodiments.

FIG. 12 illustrates an example method by which embodiments of the present disclosure can be fabricated. FIGS. 13-25 illustrate views of various stages of fabrication of the example method depicted in FIG. 12. Concurrent reference to FIG. 12 and FIGS. 13-25 will facilitate explanation.

The method 1200 is an example method for collecting a bundle of nanofibers together that, upon insertion into a tube, will expand within the tube and have an inter-fiber spacing that will facilitate nerve regrowth, as described above.

Figure 13:
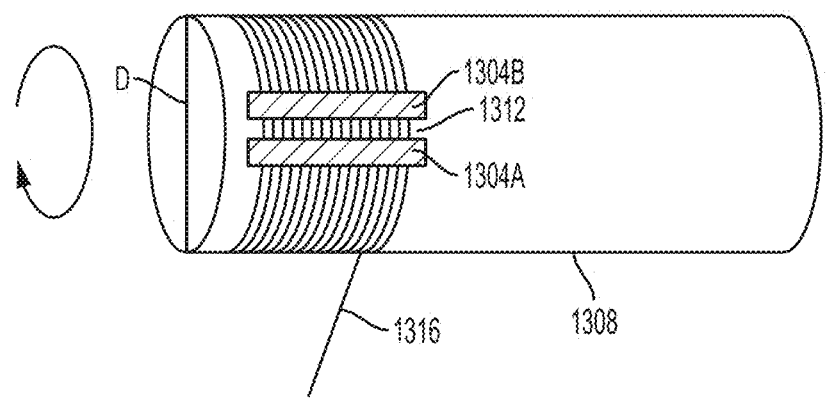
FIG. 13-25 are schematic illustrations of an example method for forming a bundle of aligned segments of the nanofiber yarn on a roller and disposing the bundle within a tube, in an embodiment.

The method 1200 includes disposing 1204 at least two strips of adhesive 1304A and 1304B (collectively, 1304) on a roller 1308, as shown in FIG. 13. The adhesive strips 1304 and the roller 1308 improve the convenience of bundling nanofibers together in a quantity and configuration that will expand to fill a tube of any desired diameter while still providing the inter-fiber spacing to facilitate regeneration of nerve, as described above. This bundling is accomplished by causing the roller 1308 of a diameter D to rotate in a direction (indicated by an arrow in FIG. 13) while wrapping one or more nanofiber yarns 1316 around it.

The two strips of adhesive 1304 will, as described below, immobilize two areas of a bundle, thus improving the ability to manipulate the bundles during processing. The two strips 1304 can be separated from one another to define a gap 1312 therebetween. The dimension of the strips can vary based on many factors including the size of the roller and the quantity of nanofiber yarn to be collected (which is proportional to the number of turns of the yarn around the roller and the diameter of the roller). In some embodiments, the length of the strip can be in the range of about 1 mm to about 1000 mm (or higher depending on the diameter of the yarn and the number of turns of the roller), while the width of the strip can be in the range of about 5 mm to 100 mm. In one example, a 14.5 mm diameter yarn was wound around the roller 1308 4000 times, spanning a length of an adhesive strip of from 55 mm to 65 mm to ultimately produce a nerve scaffold with 8000 aligned segments of nanofiber yarn and with a packing density of 65%. In another example, a 14.5 mm diameter yarn was wound around the roller 1308 80 times, spanning a length of an adhesive strip of from 1.0 mm to 1.2 mm to ultimately produce a nerve scaffold with 190 aligned segments of nanofiber yarn and a packing density of 2%.

For the two strips of adhesive 1304, any kind of adhesive can be used. For example, the adhesive 1304 can include the use of an adhesive tape, or an adhesive on any of a variety of combinations of backing materials coated with the adhesive. In one embodiment, the strip of adhesive can be a pressure-sensitive tape. The pressure sensitive tape comprises a pressure-sensitive adhesive coated onto a backing material such as paper, plastic film, fabric or metal foil. The pressure-sensitive adhesive sticks on a surface by application of pressure, without heat or solvent activation. In another example, the adhesive 1304 can include a "non-carrier adhesive" layer that is placed on the roller 1308 or on an intervening substrate (such as a polymer film). A non-carrier adhesive layer is a strip of self-supporting adhesive that is not disposed on a polymer backing, but rather can be directly applied to any surface (e.g., a flexible substrate disposed on the roller 1308).

The gap 1312 is a space defined by (and between) the two strips 1304. The gap 1312 provides a location where the nanofibers wrapped around the roller can be cut and removed from the roller while their ends are immobilized by adhesion to the strips 1304. In this way, the bundle as a whole can be handled conveniently. This enables further processing of the cut nanofiber yarns into a bundle of nanofiber yarn to be used in a scaffold for nerve repair/regrowth. The gap 1312 should be sufficient to accommodate the blade/cutting technology while not separating the yarns from the adhesive. In some embodiments, the gap 1312 can be in the range of 1 mm to 50 mm. It will be appreciated that in some examples, a gap as defined by two strips is not needed and a single strip of adhesive can be used instead. The strip of adhesive (along with the nanofiber adhered over the strip) can be cut into two parts, and removed from the roller while ends of nanofibers are fixed to two parts of the adhesive strip.

The roller 1308 can be a cross-section of a circular or an elliptical cylinder around which a bundle of aligned nanofiber yarn can be wrapped. The size of the roller is defined by its diameter D. The diameter D is a factor used to determine a length of the bundle of nanofiber yarn to be collected. Examples of a roller with a large diameter D will produce a bundle of long nanofiber yarns (after cutting), while other examples of a roller with a small diameter D will produce a bundle of short nanofiber yarns (after cutting). In some embodiments, the diameter D can be in the range of about 10 cm to 3 m.

The volume of nanofibers in the bundle can be a function of the number of revolutions of nanofiber yarn around the roller 1308. Each revolution of yarn corresponds to a linear distance of the yarn that is a function of the circumference of the roller. A roller with a greater number of revolutions of nanofiber yarn will produce a bundle of with many nanofibers, while the same sized roller with fewer revolutions of nanofiber yarn will produce a bundle with fewer of nanofibers. In some embodiments, the number of turns of nanofiber yarn around the roller can be from 10 to 100,000. In one embodiment, the number of turns of nanofiber yarn is from 2000 to 4000.

Once the two strips of adhesive are disposed 1204 on the roller 1308, a nanofiber yarn can be wrapped 1208 around the roller by causing the roller to rotate (e.g., as indicted by the arrow in FIG. 13). The nanofiber 1316 can be wrapped around a portion of the roller so as to contact the two strips of adhesive. As indicated above, the adhesive strips facilitate removal of the bundle of nanofibers from the roller 1308.

In some embodiments, the nanofiber yarns can be wrapped around the roller while applying tension to the yarn. Maintaining tension on the yarn while wrapping improves the alignment of nanofiber yarn on the roller. Alignment of the nanofiber can also be further improved by rotating the roller at a slower rate in some examples. The volume of the nanofibers in the bundle can also be a function of tension on a yarn during winding. Yarn wound around the roller under a tensile force may have a lower bundle volume than yarn wound around the roller under little or no tensile force because yarns at low or no tension can be less aligned and can occupy more space. In some examples, tension can be applied to the nanofiber yarns by employing a bobbin that maintains a tensile force on the yarn as it is rolled onto the roller. In some other examples, a guide can be configured to provide tension to the nanofiber yarns or tension can be applied using a pulley system. Applied tension can be great enough to cause alignment between nanofiber yarns and less than an ultimate tensile strength of the yarn.

Figure 14:
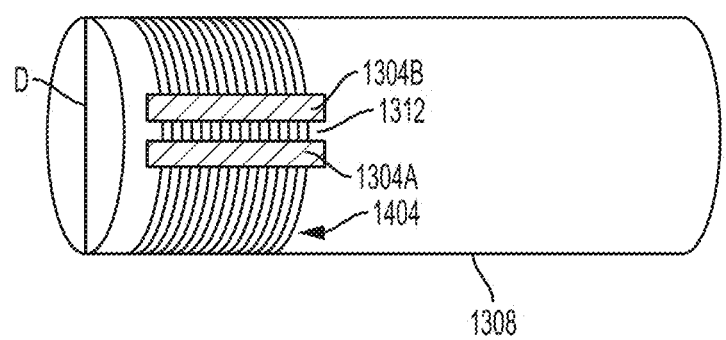
Figure 15:
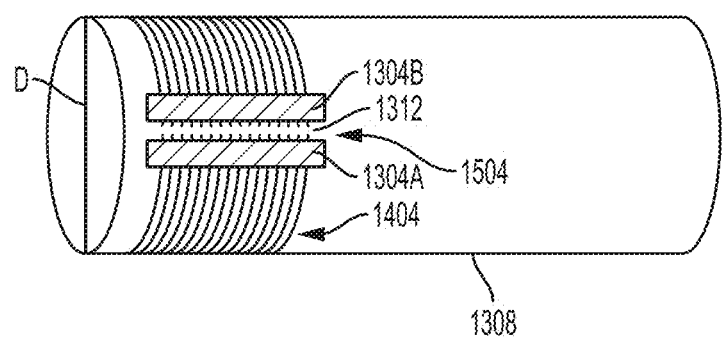

Referring to FIG. 14, once the nanofiber yarns are wrapped 1208 around the roller, a bundle of aligned segments of the nanofiber yarn 1404 is formed 1212 on the roller 1308. The bundle 1404 of nanofiber yarns is a collection of aligned nanofiber yarns whose two ends are fixed at two strips of adhesive 1304. As discussed above, the length of the bundle will be proportional to the circumference of the roller 1308, while the volume of the bundle and the number of segments of yarn within the bundle will be proportional to the number of times the nanofiber yarn is wound around the roller. The length of the bundle 1404 that is desired may be influenced by factors such as the size of a nerve scaffold to be manufactured, size of a nerve injury to be repaired, and length of the gap between the severed ends of the nerve to be regenerated. The volume of the bundle 1404 may be influenced by factors such as the diameter of a tube (as described below), percentage volume of the tube to be filled with nanofibers, and number of folds each of the bundle will undergo prior to disposing 1228 the bundle into the tube.

Once the bundle of nanofiber yarns 1404 is formed 1212 around the roller 1308, the bundle of yarns is separated 1216 or severed at the gap 1312. This separation is indicated by the arrow 1504 in FIG. 15. The ends of the bundle can be further separated 1216 from one another to form a linear configuration of the bundle. In examples where a single broad strip of adhesive is used, in lieu of two strips of adhesive, the broad strip of adhesive together with the bundle of nanofiber yarns fixed on the strip is cut and the ends separated.

Various technology can be applied to cut the bundle 1404 of nanofiber yarns including precision blades, lasers, among others. The bundle 1404 of nanofiber yarns is cut in such as a way that the nanofiber yarns remain fixed at the two strips of adhesive 1304. In embodiments where a single broad strip of adhesive is used (instead of two strips of adhesive), a single cutting technology or two different cutting technologies can be applied to cut the strip of adhesive and the bundle 1404 of nanofiber yarns.

Figure 16:
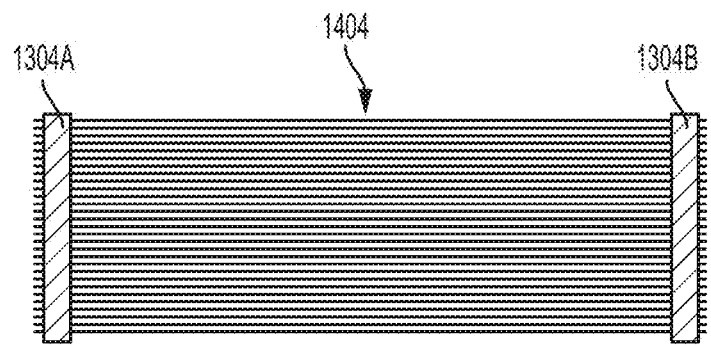
Figure 17:
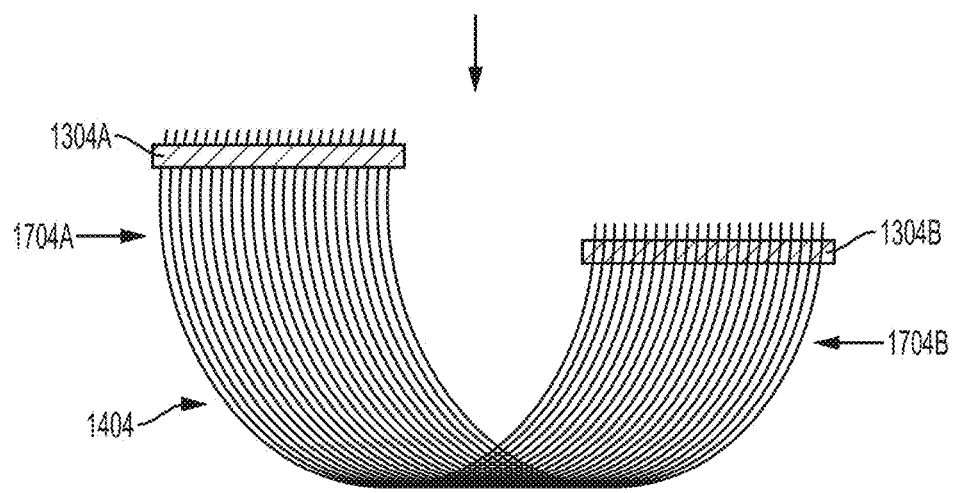

Once separated 1216, the bundle 1404 of the nanofiber yarn is removed 1220 from the roller 1308, as shown in FIG. 16.

After removing 1220 the bundle 1404 of nanofiber yarn from the roller 1308, the bundle 1404 can be folded 1224 into half (or some other sub-unit) of its original length. Folding 1224 of the bundle 1404 of nanofiber yarn can be achieved by bringing the two ends (in this example corresponding to adhesive strips 1304A, 1304B), as indicated by arrows 1704A and 1704B in FIG. 17.

Figure 18:
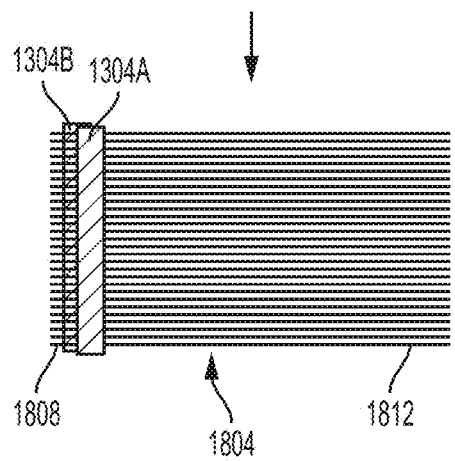

Folding of bundle 1404 of nanofiber in half produces a folded bundle 1804 of nanofiber yarns, as shown in FIG. 18. The folded bundle 1804 doubles the number of nanofiber yarns per unit length compared to that of the bundle 1404. The folded bundle 1804 of nanofiber yarn comprises two ends—a first end 1808 defined by two strips of adhesive layered over each other, and a second end 1812 defined by folded bundle of nanofiber yarns without support of a strip of adhesive.

Figure 19:
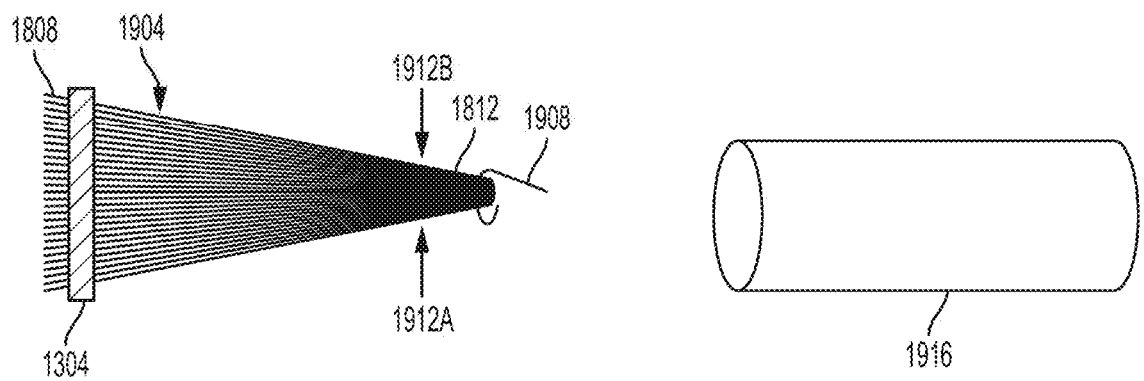
Figure 20:
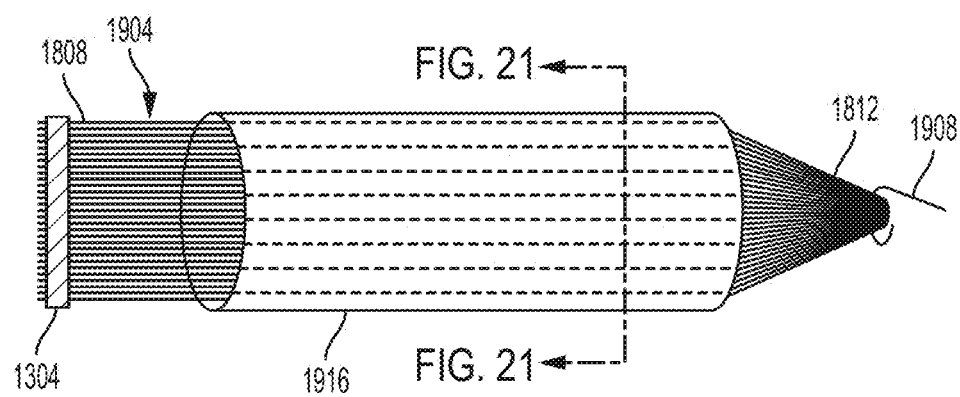
Figure 21:
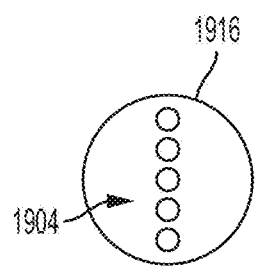
Figure 22:
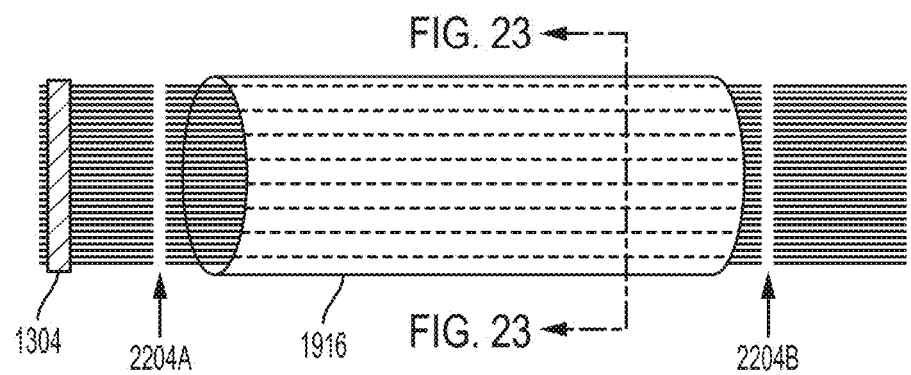

Once the folding 1224 of the bundle 1404 of nanofiber yarn is achieved, the folded bundle 1804 can be further processed so as to dispose the bundle of the nanofiber yarn within a tube 1916. In order to dispose 1228 the folded bundle 1804 into the tube, the second end 1812 of the bundle can be threaded to converge (as indicated by arrows 1912A and 1912B) the nanofiber yarns to a narrower grouping. Converging all the nanofiber yarns together enables the folded bundle 1904 to be drawn through, placed within, or threaded into the tube 1916, as shown in FIGS. 19-21. The threading can be achieved in many ways including, but not limited to, by using a needle or a hook 1908, as shown in FIG. 19.

The example hollow tube nerve scaffold 1916, as described above and, can be a cross-section of a cylindrical or an elliptical or a polygonal tube configured to receive a bundle 1904 of nanofiber yarn that will expand to fill the tube 1916 while still providing the inter-fiber spacing to facilitate regeneration of nerve.

FIG. 20 is a perspective view of an example tube 1916 within which the bundle 1904 of nanofiber yarns has been disposed 1228. Disposing 1228 of the bundle 1904 within the tube 1916 results in enclosing a middle portion of the bundle 1904 within the tube while leaving the two ends of the bundle 1904 outside the tube 2004. FIG. 21 is a cross-sectional view of tube 1916 enclosing the bundle 1904 of nanofiber yarns. The nanofibers yarns are shown to be aligned and localized within the tube 1916.

Figure 23:
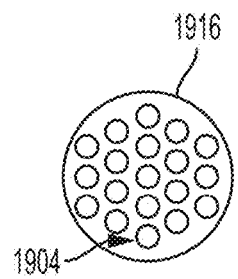
Figure 24:
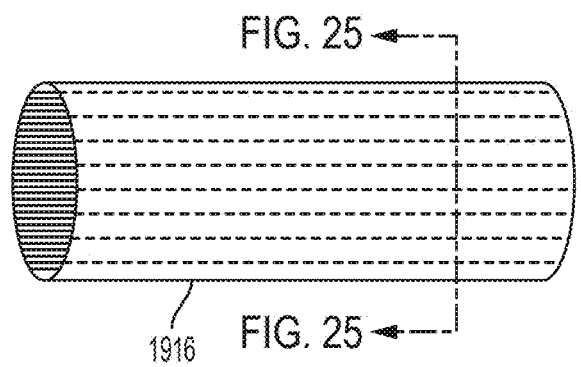
Figure 25:
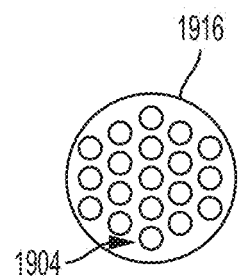

Once the bundle 1904 of nanofiber yarns is disposed 1228 within the tube 1916, two ends of the bundle 1904 on both sides of the tube can be cut (as indicated by arrows 2204A and 2204B), causing 1232 the bundle of nanofibers to expand to fill the cross-section of the tube due to the newly freed end as shown in FIGS. 22-25. FIGS. 23 and 25 are a cross-sectional view of the tube 1916 enclosing nanofibers uniformly distributed throughout the tube.

Carbon Nanofiber Nerve Scaffold

As mentioned above, some nerve scaffold tubes (e.g., tube 304) are fabricated from biologically compatible polymers and/or bioresorbable materials (e.g., silicone). In some cases, even polymers selected for their flexibility and compliance are still stiff enough to cause discomfort to a patient when used in a nerve scaffold device (e.g., because the polymer tube is more rigid than surrounding tissue). Also, in some cases tubes formed from non-bioresorbable materials may need to be surgically removed after regeneration of the nerve. This additional surgery leads to increased patient inconvenience, expense, and risk. Alternatively, a bioresorbable material can be used for a tube, but these materials can be expensive.

In embodiments described herein, a flexible, compliant, biologically compatible and/or bioresorbable tube can be fabricated using commercially available bioresorbable suture material and carbon nanofibers sheets (described below). An example structure of a nerve scaffold that includes a bundle of carbon nanofibers, as described above, within a nerve scaffold tube formed from bioresorbable suture material and carbon nanofibers sheets is illustrated in FIG. 26.

Figure 26:
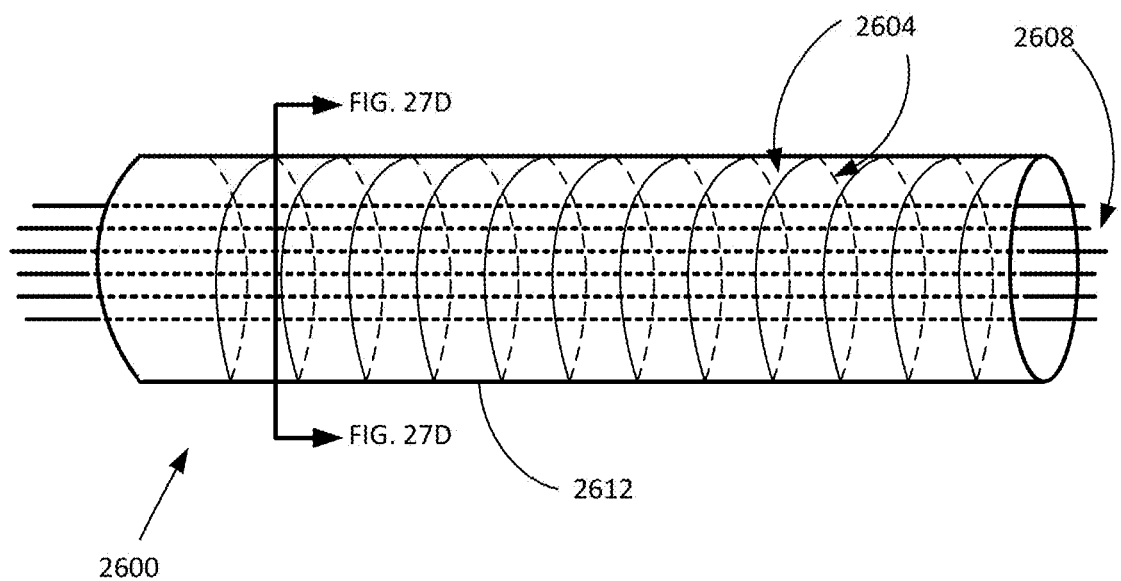
FIG. 26 is side view of a carbon nanofiber nerve scaffold, in an embodiment.

The example embodiment of a carbon nanofiber nerve scaffold 2600 illustrated in FIG. 26 includes a bioresorbable helix 2604, a bundle of carbon nanofiber yarns 2608, and a cylindrical carbon nanofiber sheet 2612.

The bioresorbable helix 2604 in some embodiment temporarily maintains a shape of the bundle of nanofiber yarns 2608. The bioresorbable helix 2604 can be formed from a thread or yarn of, for example, surgical thread (e.g., suture material) that can gradually decompose after insertion within a body. Examples of bioresorbable helix 2604 include, but are not limited to, fibers and/or yarns of polyglycolic acid, polylactic acid, polycaprolactone, collagen and polymers thereof, among other materials used for surgical sutures. In some examples, the helix 2604 can provide a form that maintains a shape and diameter of the scaffold 2600 as a whole, thus preventing (or resisting) a collapse or constriction in the cross-section of scaffold 2600 that would inhibit nerve regrowth, as will be appreciated in light of the present disclosure.

In some examples, the helix 2604 may be formed by a first helix wrapped around the cylindrical substrate 2704 in a first direction (e.g., right hand) and a second helix (e.g., left hand) opposite wrapped around the cylindrical substrate 2704 in the opposite direction. In some examples, the helix 2604 can be heated while on the substrate 2704, for example at 50%, 60%, 70%, or 80% of the glass transition temperature ($T_g$) of the constituent polymer material used to form the helix 2604. In still other examples, the helix 2604 can be formed from a braided, knitted, or crocheted tubular structure that provides the rigidity needed to maintain the spacing between the nanofibers of the bundle 2608, as described herein.

A carbon nanofiber sheet 2612 can be wrapped around the structure formed by the nanofiber yarn bundle 2608 and helix 2604. The carbon nanofiber sheet 2612 can help maintain the shape of the helix 2604 and also help maintain the confining bias the helix 2604 applies to the nanofiber yarn bundle 2608. Maintaining the structure of the bundle 2608, and more specifically the relative distances and positions of the individual nanofiber yarns within the bundle 2608 relative to one another, can facilitate nerve regrowth, as described above.

Because the helix 2604 is fabricated from a material composed to dissolve within the body slowly over time, and because the windings of the helix 2604 enable flexibility and compliance (e.g., in response to movement), the helix 2604 provides greater patient comfort than some other polymeric tubes. Furthermore, the helix 2604 does not require surgical removal because of its resorbable composition.

Figure 27A:
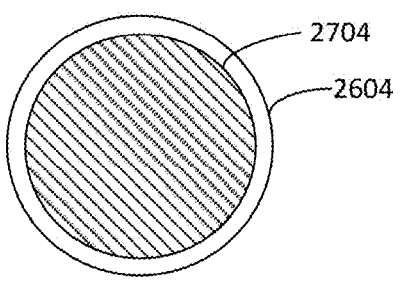
FIGS. 27A-27D are cross-sectional views illustrated example stages of progressive fabrication of the carbon nanofiber nerve scaffold depicted in FIG. 26, in embodiments.

FIGS. 27A-27D illustrate stages of fabrication of a carbon nanofiber nerve scaffold 2600 in one example. As shown in FIG. 27A, a cylindrical substrate 2704 can be provided, around which a biocompatible and/or bioresorbable yarn (or fiber) is wrapped to form helix 2604. The cylindrical substrate 2704 enables the biocompatible and/or bioresorbable yarn (or fiber) to be formed into the helix 2604 configuration, as shown in FIG. 26.

Figure 27B:
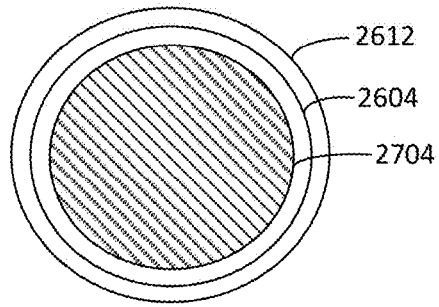
Figure 27C:
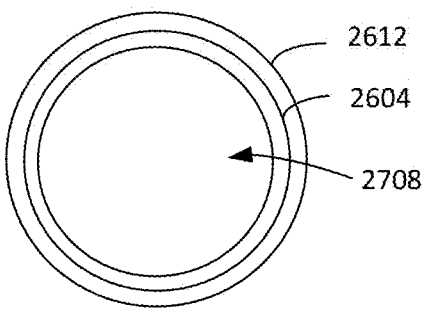
Figure 27D:
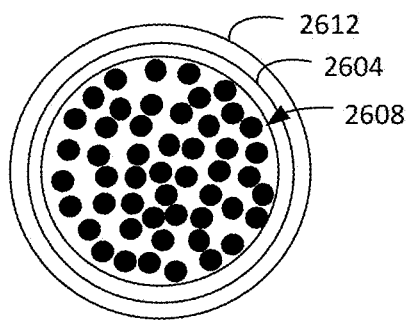

FIG. 27B illustrates the wrapping of the helix 2604 with a carbon nanofiber sheet 2612. In some examples, the carbon nanofiber sheet 2612 can be infiltrated with a polymer (e.g., using a solution of a solvent and a biocompatible and/or bioresorbable polymer, where the solvent is removed after application to the sheet). Regardless, the cylindrical substrate 2704 can then be removed after application of the sheet 2612, as shown in FIG. 27C. The cylindrical vacancy 2708, formed by removal of the cylindrical substrate 2704, is defined by one or more of the helix 2604 and/or the nanofiber sheet 2612. The vacancy 2708 can then be used to host the bundle of nanofiber yarns 2608.

The bundle of carbon nanofiber yarns 2608 disposed within an interior of the helix 2604 includes any of the previously described embodiments, and needs no further description. Similarly, the carbon nanofiber sheet 2612 that is wrapped around the helix 2604 and yarns 2608 is described below.

The carbon nanofiber nerve scaffold 2600 can be formed by, in one example, helically wrapping Nanofiber Forests As used herein, the term "nanofiber" means a fiber having a diameter less than 1 µm. While the embodiments herein are primarily described as fabricated from carbon nanotubes, it will be appreciated that other carbon allotropes, whether graphene, micron or nano-scale graphite fibers and/or plates, and even other compositions of nano-scale fibers such as boron nitride may be densified using the techniques described below. As used herein, the terms "nanofiber" and "carbon nanotube" encompass both single walled carbon nanotubes and/or multi-walled carbon nanotubes in which carbon atoms are linked together to form a cylindrical structure. In some embodiments, carbon nanotubes as referenced herein have between 4 and 10 walls. As used herein, a "nanofiber sheet" or simply "sheet" refers to a sheet of nanofibers aligned via a drawing process (as described in PCT Publication No. WO 2007/015710, and incorporated by reference herein in its entirety) so that a longitudinal axis of a nanofiber of the sheet is parallel to a major surface of the sheet, rather than perpendicular to the major surface of the sheet (i.e., in the as-deposited form of the sheet, often referred to as a "forest"). This is illustrated and shown in FIGS. 30 and 31, respectively.

The dimensions of carbon nanotubes can vary greatly depending on production methods used. For example, the diameter of a carbon nanotube may be from 0.4 nm to 100 nm and its length may range from 10 µm to greater than 55.5 cm. Carbon nanotubes are also capable of having very high aspect ratios (ratio of length to diameter) with some as high as 132,000,000:1 or more. Given the wide range of dimensional possibilities, the properties of carbon nanotubes are highly adjustable, or "tunable." While many intriguing properties of carbon nanotubes have been identified, harnessing the properties of carbon nanotubes in practical applications requires scalable and controllable production methods that allow the features of the carbon nanotubes to be maintained or enhanced.

Due to their unique structure, carbon nanotubes possess particular mechanical, electrical, chemical, thermal and optical properties that make them well-suited for certain applications. In particular, carbon nanotubes exhibit superior electrical conductivity, high mechanical strength, good thermal stability and are also hydrophobic. In addition to these properties, carbon nanotubes may also exhibit useful optical properties. For example, carbon nanotubes may be used in light-emitting diodes (LEDs) and photo-detectors to emit or detect light at narrowly selected wavelengths. Carbon nanotubes may also prove useful for photon transport and/or phonon transport.

Figure 28:
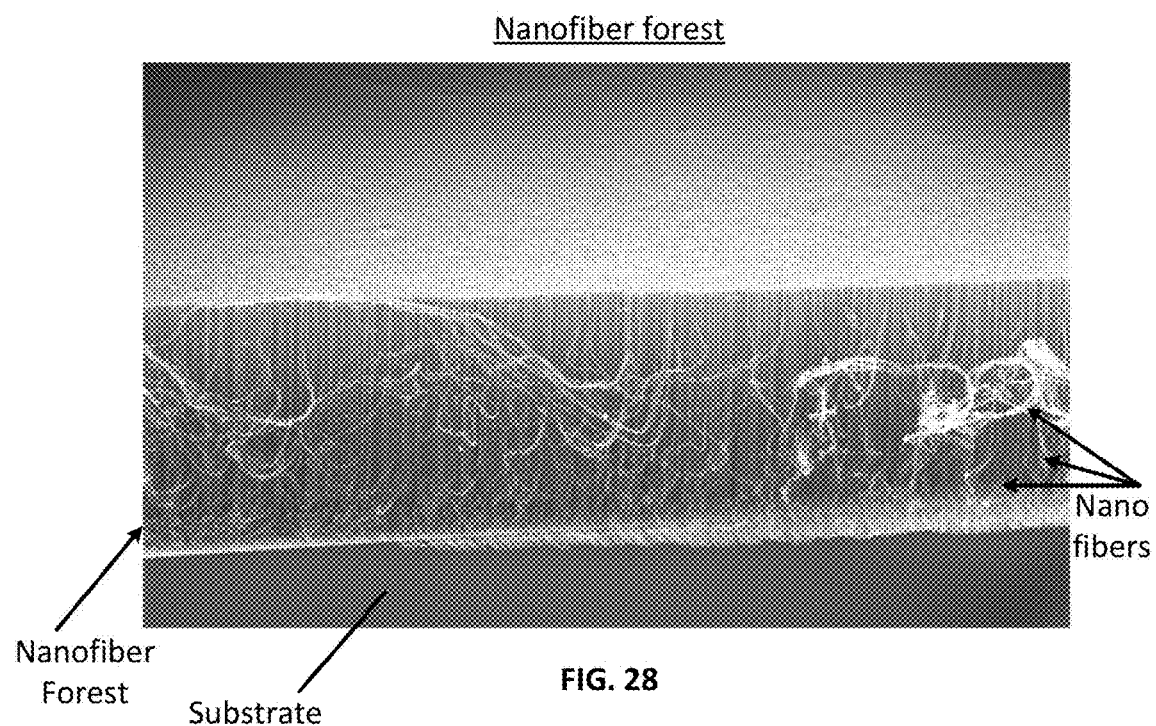
FIG. 28 is a photomicrograph of an example forest of nanofibers on a substrate, in an embodiment.

In accordance with various embodiments of the subject disclosure, nanofibers (including but not limited to carbon nanotubes) can be arranged in various configurations, including in a configuration referred to herein as a "forest." As used herein, a "forest" of nanofibers or carbon nanotubes refers to an array of nanofibers having approximately equivalent dimensions that are arranged substantially parallel to one another on a substrate. FIG. 28 shows an example forest of nanofibers on a substrate. The substrate may be any shape but in some embodiments the substrate has a planar surface on which the forest is assembled. As can be seen in FIG. 28, the nanofibers in the forest may be approximately equal in height and/or diameter.

Nanofiber forests as disclosed herein may be relatively dense. Specifically, the disclosed nanofiber forests may have a density of at least 1 billion nanofibers/cm$^2$. In some specific embodiments, a nanofiber forest as described herein may have a density of between 10 billion/cm$^2$ and 30 billion/cm$^2$. In other examples, the nanofiber forest as described herein may have a density in the range of 90 billion nanofibers/cm$^2$. The forest may include areas of high density or low density and specific areas may be void of nanofibers. The nanofibers within a forest may also exhibit inter-fiber connectivity. For example, neighboring nanofibers within a nanofiber forest may be attracted to one another by van der Waals forces. Regardless, a density of nanofibers within a forest can be increased by applying techniques described herein.

Methods of fabricating a nanofiber forest are described in, for example, PCT No. WO2007/015710, which is incorporated herein by reference in its entirety.

Figure 29:
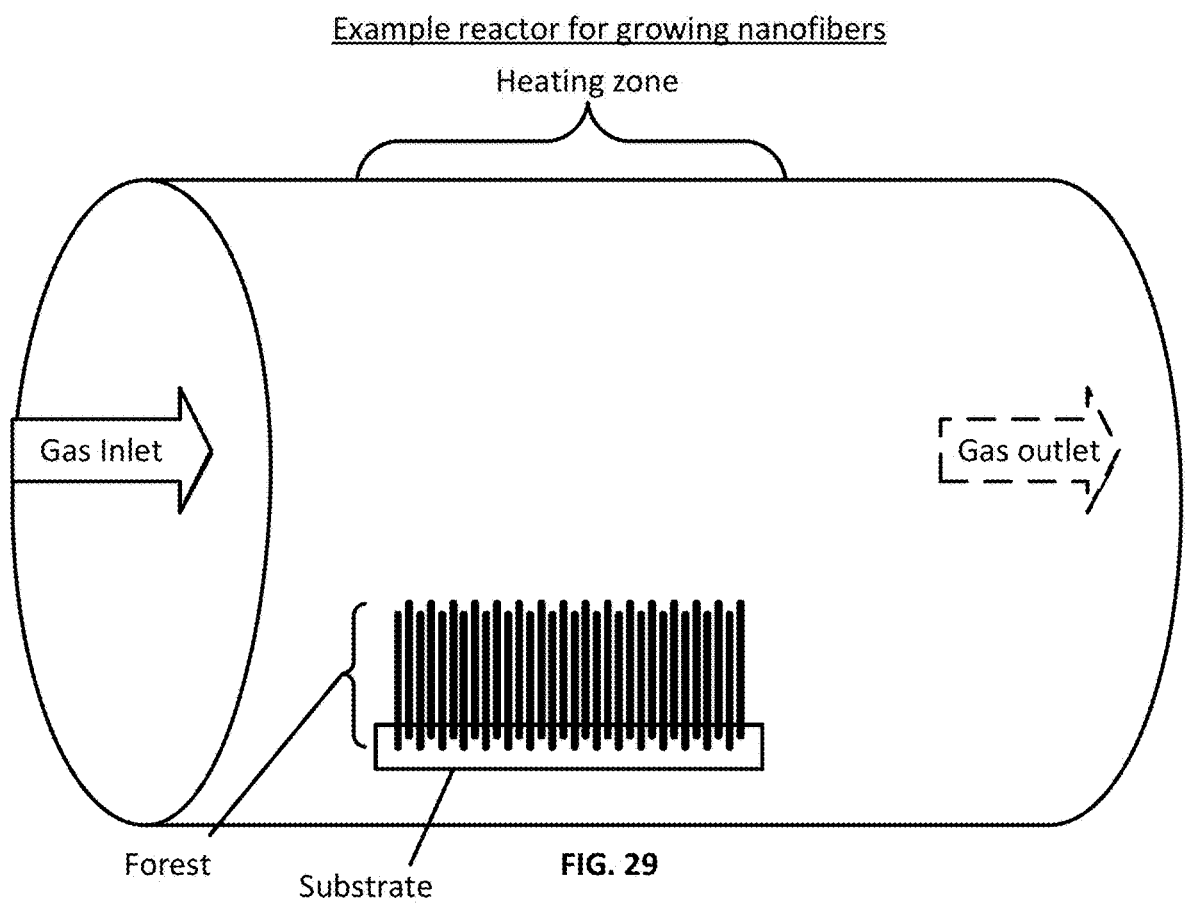
FIG. 29 is a schematic illustration of an example reactor for nanofiber growth, in an embodiment.

Various methods can be used to produce nanofiber precursor forests. For example, in some embodiments nanofibers may be grown in a high-temperature furnace, schematically illustrated in FIG. 29. In some embodiments, catalyst may be deposited on a substrate, placed in a reactor and then may be exposed to a fuel compound that is supplied to the reactor. Substrates can withstand temperatures of greater than 800° C. or even 1000° C. and may be inert materials. The substrate may comprise stainless steel or aluminum disposed on an underlying silicon (Si) wafer, although other ceramic substrates may be used in place of the Si wafer (e.g., alumina, zirconia, SiO2, glass ceramics). In examples where the nanofibers of the precursor forest are carbon nanotubes, carbon-based compounds, such as acetylene may be used as fuel compounds. After being introduced to the reactor, the fuel compound(s) may then begin to accumulate on the catalyst and may assemble by growing upward from the substrate to form a forest of nanofibers. The reactor also may include a gas inlet where fuel compound(s) and carrier gasses may be supplied to the reactor and a gas outlet where expended fuel compounds and carrier gases may be released from the reactor. Examples of carrier gases include hydrogen, argon, and helium. These gases, in particular hydrogen, may also be introduced to the reactor to facilitate growth of the nanofiber forest. Additionally, dopants to be incorporated in the nanofibers may be added to the gas stream.

In a process used to fabricate a multilayered nanofiber forest, one nanofiber forest is formed on a substrate followed by the growth of a second nanofiber forest in contact with the first nanofiber forest. Multi-layered nanofiber forests can be formed by numerous suitable methods, such as by forming a first nanofiber forest on the substrate, depositing catalyst on the first nanofiber forest and then introducing additional fuel compound to the reactor to encourage growth of a second nanofiber forest from the catalyst positioned on the first nanofiber forest. Depending on the growth methodology applied, the type of catalyst, and the location of the catalyst, the second nanofiber layer may either grow on top of the first nanofiber layer or, after refreshing the catalyst, for example with hydrogen gas, grow directly on the substrate thus growing under the first nanofiber layer. Regardless, the second nanofiber forest can be aligned approximately end-to-end with the nanofibers of the first nanofiber forest although there is a readily detectable interface between the first and second forest. Multi-layered nanofiber forests may include any number of forests. For example, a multi-layered precursor forest may include two, three, four, five or more forests.

Nanofiber Sheets

Figure 30:
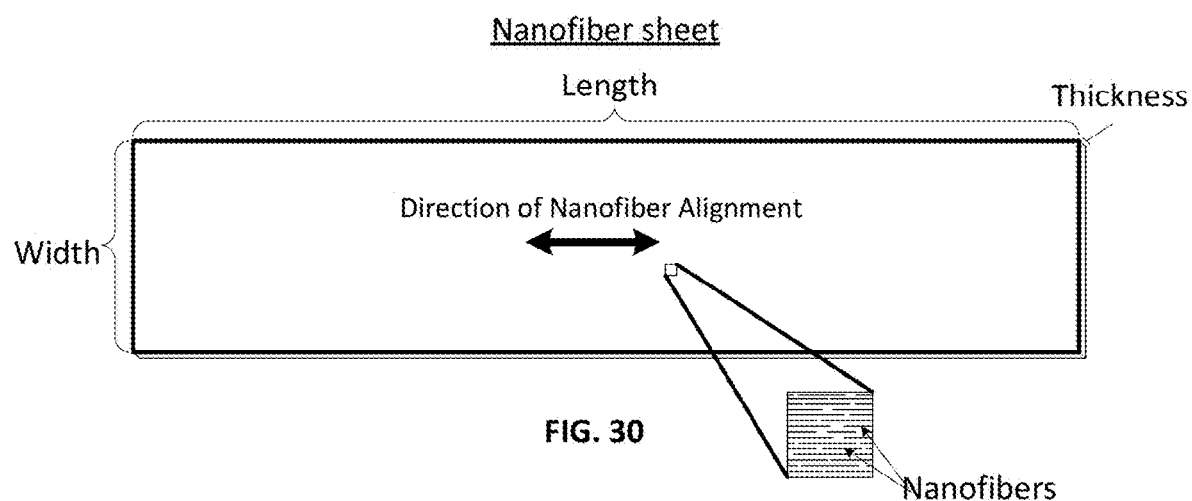
FIG. 30 is a schematic illustration of a nanofiber sheet that identifies relative dimensions of the sheet and schematically illustrates nanofibers within the sheet aligned end-to-end in a plane parallel to a surface of the sheet, in an embodiment.

In addition to arrangement in a forest configuration, the nanofibers of the subject application may also be arranged in a sheet configuration. As used herein, the term "nanofiber sheet," "nanotube sheet," or simply "sheet" refers to an arrangement of nanofibers where the nanofibers are aligned end to end in a plane. An illustration of an example nanofiber sheet is shown in FIG. 30 with labels of the dimensions. In some embodiments, the sheet has a length and/or width that is more than 100 times greater than the thickness of the sheet. In some embodiments, the length, width or both, are more than $10^3$, $10^6$ or $10^9$ times greater than the average thickness of the sheet. A nanofiber sheet can have a thickness of, for example, between approximately 5 nm and 30 μm and any length and width that are suitable for the intended application. In some embodiments, a nanofiber sheet may have a length of between 1 cm and 10 meters and a width between 1 cm and 1 meter. These lengths are provided merely for illustration. The length and width of a nanofiber sheet are constrained by the configuration of the manufacturing equipment and not by the physical or chemical properties of any of the nanotubes, forest, or nanofiber sheet. For example, continuous processes can produce sheets of any length. These sheets can be wound onto a roll as they are produced.

As can be seen in FIG. 30, the axis in which the nanofibers are aligned end-to end is referred to as the direction of nanofiber alignment. In some embodiments, the direction of nanofiber alignment may be continuous throughout an entire nanofiber sheet. Nanofibers are not necessarily perfectly parallel to each other and it is understood that the direction of nanofiber alignment is an average or general measure of the direction of alignment of the nanofibers.

Nanofiber sheets may be assembled using any type of suitable process capable of producing the sheet. In some example embodiments, nanofiber sheets may be drawn from a nanofiber forest. An example of a nanofiber sheet being drawn from a nanofiber forest is shown in FIG. 31

Figure 31:
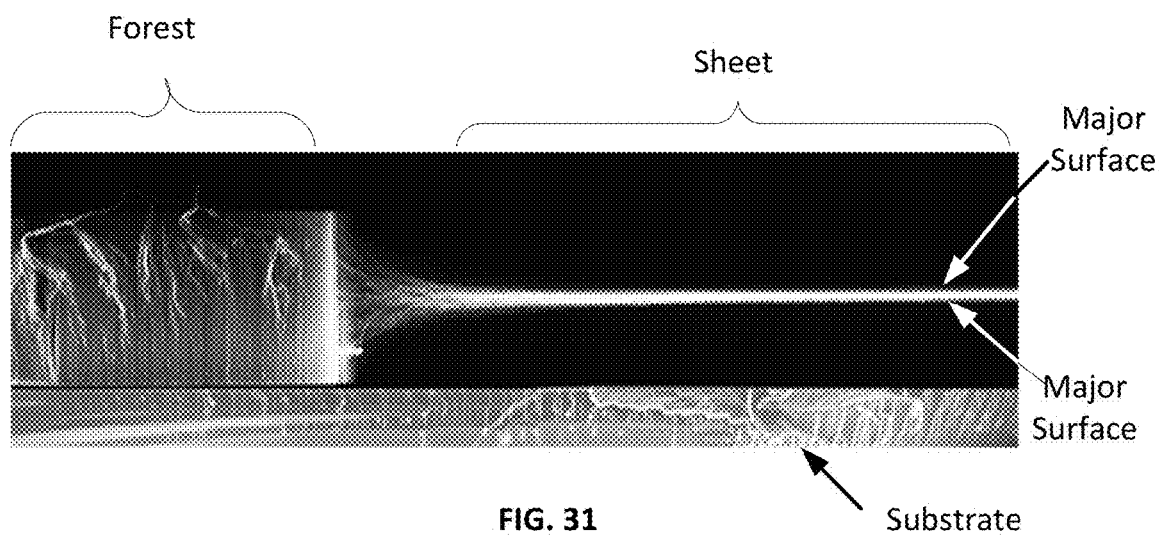
FIG. 31 is an SEM photomicrograph is an image of a nanofiber sheet being laterally drawn from a nanofiber forest, the nanofibers aligning from end-to-end as schematically shown in FIG. 28, in an embodiment.

As can be seen in FIG. 31, the nanofibers may be drawn laterally from the forest and then align end-to-end to form a nanofiber sheet. In embodiments where a nanofiber sheet is drawn from a nanofiber forest, the dimensions of the forest may be controlled to form a nanofiber sheet having particular dimensions. For example, the width of the nanofiber sheet may be approximately equal to the width of the nanofiber forest from which the sheet was drawn. Additionally, the length of the sheet can be controlled, for example, by concluding the draw process when the desired sheet length has been achieved.

Nanofiber sheets have many properties that can be exploited for various applications. For example, nanofiber sheets may have tunable opacity, high mechanical strength and flexibility, thermal and electrical conductivity, and may also exhibit hydrophobicity. Given the high degree of alignment of the nanofibers within a sheet, a nanofiber sheet may be extremely thin. In some examples, a nanofiber sheet is on the order of approximately 10 nm thick (as measured within normal measurement tolerances), rendering it nearly two-dimensional. In other examples, the thickness of a nanofiber sheet can be as high as 200 nm or 300 nm. As such, nanofiber sheets may add minimal additional thickness to a component.

As with nanofiber forests, the nanofibers in a nanofibers sheet may be functionalized by a treatment agent by adding chemical groups or elements to a surface of the nanofibers of the sheet and that provide a different chemical activity than the nanofibers alone. Functionalization of a nanofiber sheet can be performed on previously functionalized nanofibers or can be performed on previously unfunctionalized nanofibers. Functionalization can be performed using any of the techniques described herein including, but not limited to CVD, and various doping techniques.

Nanofiber sheets, as drawn from a nanofiber forest, may also have high purity, wherein more than 90%, more than 95% or more than 99% of the weight percent of the nanofiber sheet is attributable to nanofibers, in some instances. Similarly, the nanofiber sheet may comprise more than 90%, more than 95%, more than 99% or more than 99.9% by weight of carbon.

Further Considerations

The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the invention, which is set forth in the following claims.

What is claimed is:

1. A method of manufacturing a nerve scaffold, the method comprising:
   disposing a first strip of adhesive on a roller;
   wrapping a nanofiber yarn around the roller by rotating the roller, the wrapped nanofiber yarn forming a bundle of aligned segments of the nanofiber yarn on the roller, wherein the nanofiber yarn passes over the first strip of adhesive;
   separating the bundle of aligned segments of the nanofiber yarn by dividing the strip into two portions;
   removing the bundle aligned segments of the nanofiber yarn from the roller;
   folding the bundle of aligned segments of the nanofiber yarn, wherein the bundle includes a first end and a second end opposite to the first end; and
   configuring the bundle to be disposed within a tube.

2. The method of claim 1, further comprising disposing a second strip of adhesive on the roller, the first strip of adhesive and the second strip of adhesive defining a gap therebetween.

3. The method of claim 2, wherein separating the bundle of nanofiber yarn occurs at the gap defined by the first strip of adhesive and the second strip of adhesive.

4. The method of claim 1, wherein the bundle of aligned segments of the nanofiber yarn includes a midpoint, and wherein the folding comprises folding the bundle of the nanofiber yarn at the midpoint.

5. The method of claim 4, wherein the midpoint of the folded bundle is connected to a drawing structure, the drawing structure used for placing the folded bundle within the tube.

6. The method of claim 5, further comprising cutting the first end and second end of the folded bundle of aligned segments of nanofiber yarns.

7. The method of claim 6, wherein the cutting of the first end and the second end of the bundle of aligned segments of the nanofiber yarn causes the bundle of aligned segments of nanofiber yarns to expand to fill a cross-section of the tube.

8. The method claim 1, wherein the folded bundle includes from 1000 to 8000 aligned segments of the nanofiber yarn.

9. The method of claim 1, wherein a weight ratio of the folded bundle of the nanofiber yarn to the tube in which the folded bundle is disposed is about 0.65 to about 1.

10. The method claim 1, wherein the nanofiber yarn has a diameter of from 5 µm to 30 µm.

11. The method claim 1, wherein the nanofiber yarn has a diameter of from 13 µm to 15 µm.

12. The method of claim 1, wherein the nanofiber yarn is comprised of carbon nanotubes.

13. The method of claim 1, further comprising forming the tube by:
    forming a cylindrical helix comprising a surgical suture material, the cylindrical helix defining an interior; and
    wrapping a carbon nanofiber sheet around the cylindrical helix on a surface of the helix opposite the interior.

14. The method of claim 1, wherein the nanofiber yarn is a false twisted nanofiber yarn.

15. The method claim 1, wherein the nanofiber yarn is a single ply false twisted nanofiber yarn.

16. The method of claim 1, wherein a surface of the nanofiber yarn has an absence of surface topographic features greater than 1 µm above or below a surface of the nanofiber yarn.

17. The method of claim 1, wherein a surface of the nanofiber yarn has surface topographic features less than 0.1 µm above or below a surface of the nanofiber yarn.

18. The method of claim 1, wherein the bundle of aligned segments of nanofiber yarn occupies between 1 and 5%, 1 and 10%, 1 and 20%, 1 and 30%, 1 and 40% or 1 and 50% of a volume of the tube in which the bundle is disposed.

19. The method of claim 1, wherein an average distance between proximate aligned segments of the nanofiber yarn disposed within the tube is from 5 µm to 15 µm.

* * * * *